(12) United States Patent
Kim et al.

(10) Patent No.: US 9,387,267 B2
(45) Date of Patent: Jul. 12, 2016

(54) IODINE-CONTAINING RADIAL-SHAPED MACROMOLECULAR COMPOUNDS, PREPARATION METHOD THEREOF AND CONTRAST MEDIA COMPOSITIONS FOR CT COMPRISING THE SAME

(75) Inventors: Yoonkyung Kim, Seoul (KR);
Dong-Eog Kim, Goyang-si (KR);
Hye-Youn Jung, Daejeon (KR); Yun Hui Choe, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 400 days.

(21) Appl. No.: 13/816,846

(22) PCT Filed: Aug. 16, 2011

(86) PCT No.: PCT/KR2011/006002
§ 371 (c)(1),
(2), (4) Date: Feb. 13, 2013

(87) PCT Pub. No.: WO2012/021046
PCT Pub. Date: Feb. 16, 2012

(65) Prior Publication Data
US 2013/0150529 A1  Jun. 13, 2013

(30) Foreign Application Priority Data

Aug. 13, 2010 (KR) .................. 10-2010-0078060
Aug. 12, 2011 (KR) .................. 10-2011-0080912

(51) Int. Cl.
*A61K 51/06*  (2006.01)
*A61K 49/10*  (2006.01)
*A61K 49/12*  (2006.01)
*A61K 49/14*  (2006.01)
*A61K 49/04*  (2006.01)

(52) U.S. Cl.
CPC ............ *A61K 51/06* (2013.01); *A61K 49/0442* (2013.01)

(58) Field of Classification Search
CPC ....... A61K 51/06; A61K 49/12; A61K 49/14; A61K 49/10; A61K 49/04
USPC .......................................... 524/54.1; 525/54
See application file for complete search history.

(56) References Cited

U.S. PATENT DOCUMENTS 5,871,713 A * 2/1999 Meyer et al. ............... 424/9.452

OTHER PUBLICATIONS

Hallouard et al., "Iodinated blood pool contrast media for preclinical X-ray imaging applications—A review", (Biomaterials, 31, (2010) p. 6249-6268).*

* cited by examiner

*Primary Examiner* — Ling Choi
*Assistant Examiner* — Ronald Grinsted
(74) *Attorney, Agent, or Firm* — Lucas & Mercanti, LLP

(57) ABSTRACT

Disclosed herein is an iodine-containing radial-shaped macromolecule suitable for an active ingredient of the computed tomography (CT) contrast medium, a method to prepare the same, and a contrast medium composition including the same. With respect to the iodine-containing radial-shaped macromolecule according to the present invention, the duration of contrast enhancement has been significantly improved in comparison to that of the current small molecular contrast media compounds containing iodine.

18 Claims, 10 Drawing Sheets

IODINE-CONTAINING RADIAL-SHAPED MACROMOLECULAR COMPOUNDS, PREPARATION METHOD THEREOF AND CONTRAST MEDIA COMPOSITIONS FOR CT COMPRISING THE SAME

CROSS-REFERENCE TO RELATED APPLICATIONS

This application is a 371 of PCT/KR2011/006002, filed on Aug. 16, 2011, which claims the benefit of Korean Patent Application Nos. 10-2010-0078060 filed Aug. 13, 2010 and 10-2011-0080912 filed on Aug. 12, 2011, the contents of each of which are incorporated herein by reference.

BACKGROUND OF THE INVENTION

1. Field of the Invention

The present disclosure relates to a radial-shaped macromolecule containing iodine as an active ingredient for the computed tomography (CT) contrast medium, a method of preparing the same, and a CT contrast medium composition including the radial-shaped macromolecule.

2. Description of the Related Art

Computed tomography (CT) denotes a photographic technique in which a target area of the human body was irradiated with X-ray in various directions and the transmitted X-ray is collected with a detector, and then the difference between X-ray absorptions with respect to the area is reconstructed through a mathematical technique by using a computer. That is, it is an imaging technique producing a three-dimensional image through computer programming by recombining many two-dimensional X-ray photographs taken at various different angles with a camera rotating 360 degrees around the body.

Therefore, such X-ray-based imaging generally generates images mainly focused on bones. If the CT imaging is performed after the injection of a contrast medium based on a relatively high atomic number such as barium or iodine into the blood vessel of a living animal or human, X-ray cannot transmit clearly through the area where such contrast medium exists due to photoelectric effect, but will be absorbed to exhibit white or light grayish color on the produced images similar to the bones which is shown in very bright white color. In general, the degree ($\alpha$) of absorption of X-ray is proportional to the atomic number (N) and the wavelength ($\lambda$) of the X-ray. That is, the degree ($\alpha$) of absorption of X-ray is inversely proportional to the energy of X-ray.

$$\alpha = N^5 \lambda^{7/2}$$

CT along with magnetic resonance imaging (MRI) provides anatomical information, while PET (positron emission tomography) and SPECT (single photon emission computed tomography) imaging techniques provide information on physiological/biochemical functions. Also, despite the lower resolution of CT compared to that of MRI, CT is indispensable in clinic because of its short scan time, relatively low price for a CT scan, and good accessibility to the CT equipment as most of the hospitals own it. That is, because the total CT scan time is about one-tenth or less of the MRI scan time, CT imaging is highly indispensable particularly for emergency patients with critical brain injury requiring rapid diagnosis. Also, the patient discomfort during the MRI scan due to the noise and long scan time can be reduced by CT scan, the access to the CT equipment is facile, and the cost for a CT scan is about one-tenth of that of MRI scan.

To date, small molecular CT contrast media containing iodine used in clinic are broadly classified into two types: ionic and non-ionic compounds.

IONIC

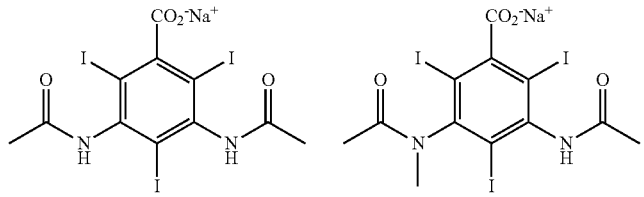

Diatrizoate
[HYPAQUE]
iodine content: 59.87%

Metrizoate
[ISOPAQUE CORONAR]
iodine content: 58.58%

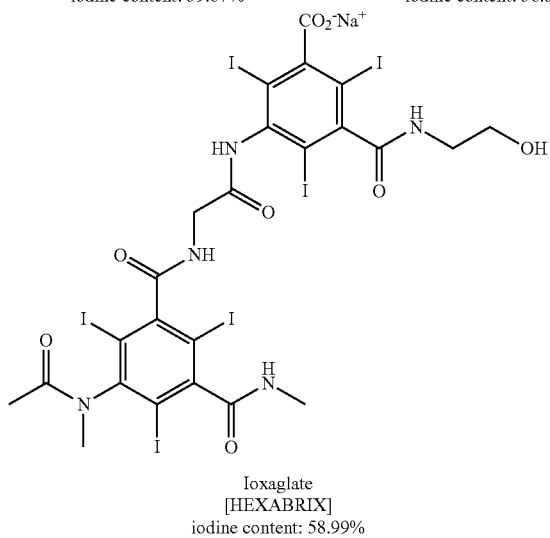

Ioxaglate
[HEXABRIX]
iodine content: 58.99%

NON-IONIC
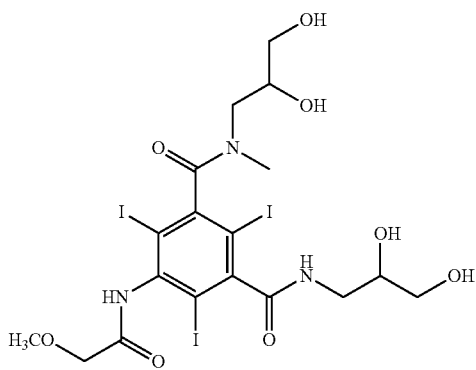
Iopromide
[ULTRAVIST]
iodine content: 48.12%
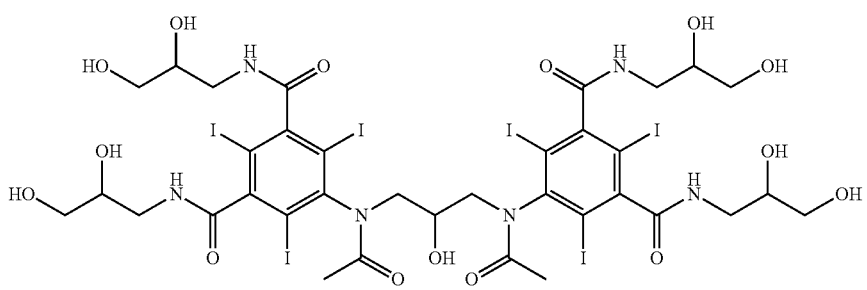
Iodixanol
[VISIPAQUE]
iodine content: 49.12%
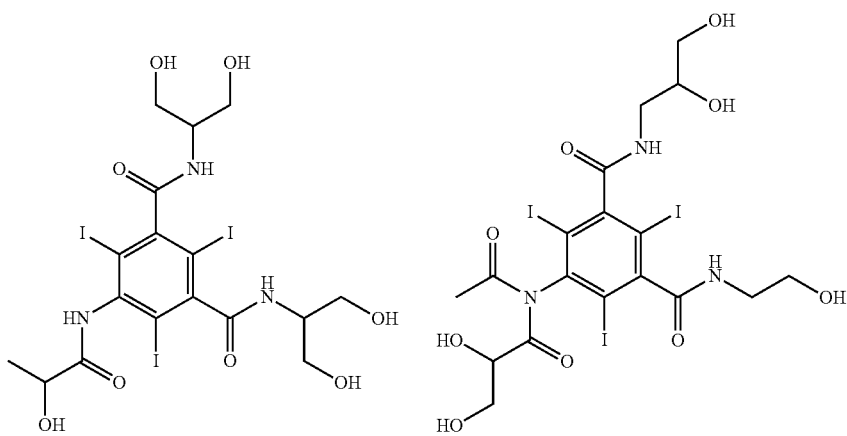
Iopromidol
[ISOVUE]
iodine content: 48.99%
Ioxilan
[OXILANT]
iodine content: 48.12%

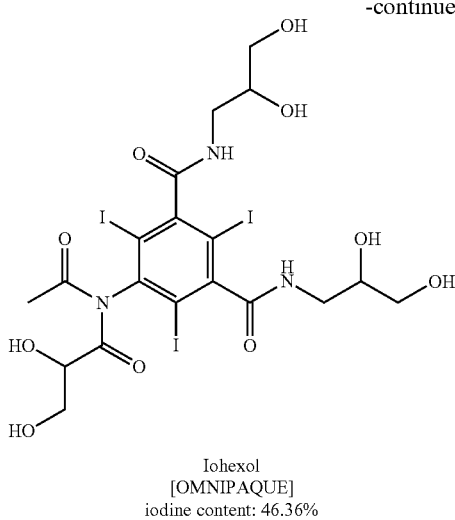

Iohexol
[OMNIPAQUE]
iodine content: 46.36%

Because the severity of side effects by the non-ionic compounds are much less than that of the ionic compounds, non-ionic CT contrast media are mostly administered these days to the patients. Also, two or three phenyl rings in the conventional small molecular non-ionic CT contrast media compounds containing iodine were linked by covalent bonds to extend the in vivo circulation time by increasing the molecular weight. However, high-dose amount for up to 80-90 g of these small molecular CT contrast media containing iodine need to be administered to adults depending on their weight in order to obtain a proper level of CT signals because of their short in vivo circulation time (half-life). Thus, adverse effects such as allergy and shock are exhibited occasionally in some patients, and in the limited worst case, life may be threatened. Such events occur more frequently when attaining sufficient circulation time is necessary by administrating high-dose amount of contrast medium for effective diagnosis of cardiovascular diseases such as the heart area. Therefore, in order to overcome these problems, there is an urgent need to develop a safer compound which can produce excellent contrast enhancement for a prolonged period by administrating relatively low-dose amount of CT contrast media. In addition, other limitations of the current small molecular CT contrast media containing iodine may include low $LD_{50}$ value, high osmolality, high viscosity, etc.

In order to overcome these limitations of small molecular CT contrast media containing iodine, the development of new macromolecular CT contrast media containing iodine has been reported recently. For example, multiple units of (commercially available) small molecular compounds containing iodine or their derivatives have been either covalently attached to the macromolecular scaffolds or physically encapsulated inside the macromolecular assemblies such as liposomes, micelles, and other nanoparticles.

Methods of encapsulating commercially available small molecular CT contrast media containing iodine or their derivatives in the macromolecular liposomes were disclosed in the Non-Patent Literatures 1 [J. Zheng, et al., Mol. Pharmaceutics 2009, 6, 571-580], 2 [A. Sachse, et al., Invest. Radiol. 1997, 32, 44-50], 3 [E. Samei, et al., Int. J. Nanomedicine 2009, 4, 277-282], and 4 [C. Y. Kao, et al., Acad. Radiol. 2003, 10, 475-483].

Methods of encapsulating commercially available small molecular CT contrast media containing iodine or their derivatives in the macromolecular micelles were disclosed in the Non-Patent Literatures 5 [V. S. Trubetskoy, et al., J. Drug Target. 1997, 4, 381-388] and 6 [V. P. Torchilin et al., Acad. Radiol. 1999, 6, 61-65]

A method of encapsulating commercially available small molecular CT contrast media containing iodine or their derivatives in the macromolecular nanoparticles was disclosed in the Non-Patent Literature 7 [F. Hyafil, et al., Nat. Med. 2007, 13, 636-641].

Regarding the Non-Patent Literature 7, the carboxylic acid end group of the iodinated compound was capped with an alkyl group to enhance the hydrophobicity of the compound, which facilitated the internalization of the iodinated compound into the interior of the nanoparticle. When these iodine-containing nanoparticles were injected into the blood vessels, generally they were readily taken up by macrophages and accumulated increasingly in the areas of inflammation, cancer, and arteriosclerosis with time where relatively larger amount of macrophages exists, to facilitate the diagnosis of related diseases by CT imaging. Meanwhile, regarding the Non-Patent Literature 5, the micellar structures were formed from the hydrophilic poly(ethylene glycol) (PEG) with its one end substituted with a short peptide containing several units of small molecular hydrophobic iodinated compounds, to extend in vivo circulation time. However, the structures of these liposomes and micelles based on self-assembly are not intact and can be easily disassembled by the changes in the surrounding media in vivo to release the entire or a portion of toxic iodinated small molecular contrast agents.

Therefore, the development of CT contrast media based on metal nanoparticles that can exhibit contrast enhancement by themselves without the need for the encapsulation of small molecular compounds containing iodine have been reported.

A CT contrast medium based on gold (Au) nanoparticles with PEG groups substituted on the surface was disclosed in the Patent Literature 1 [PCT/KR2006/003452].

A CT contrast medium based on gold nanoparticles coated with heparin was disclosed in the Non-Patent Literature 8 [I. C., Sun, et al., Chem. Eur. J. 2009, 15, 13341-13347].

A CT contrast medium based on uniformly sized tantalum (Ta) oxide nanoparticles substituted with PEG and fluorophores was disclosed in the Non-Patent Literature 9 [M. H. Oh, et al., J. Am. Chem. Soc. 2011, 133, 5508-5515].

For the CT contrast media based on metal nanoparticles, the metal (Au, Ta, etc.) itself serves as an imaging agent (i.e., absorbs X-ray beam) which was coated with biocompatible PEG and heparin to extend the in vivo circulation time and to facilitate imaging of specific organs through the accumulation in the liver, respectively.

However, the foregoing macromolecular contrast media are expected to have problems such as high costs and toxicity due to the limited excretion and long-term in vivo accumulation (i.e., half-lives of more than years to decades). Also difficulties are expected for these macromolecules in maintaining structural integrity in vivo (e.g., self-assembled structures) and achieving reproducibility in manufacturing to obtain macromolecular mixtures of the same molecular weight distribution to elicit same effects. Also, more difficulties are expected in commercializing these materials based on macromolecular mixtures for human administration through clinical testing due to the lack of standardized global protocols for toxicity evaluations.

Meanwhile, examples of liposome-based vascular contrast media for CT with encapsulated small molecular compounds containing iodine are Fenestra (ART Advanced Research Technologies Inc., Canada) and eXIA160 (Binitio Biomedical, Inc., Canada), which are both sold for animal applications only. In fact there is more pressure on the researchers in the field of basic medical research using micro-CT, not only because the price for one vial (2.5 mL) of these contrast media permitting 5-10 injections into the blood vessels of mice or rats is about one million wons, but also the injection of these contrast media into the tail vein of small animals are not easy. On the other hand, if a small molecular contrast medium for human is injected instead into the small animals, achieving a proper level of contrast enhancement is impossible because most of the contrast agents is already discharged into the bladder through kidney during the first one to three minutes of the preparation period after the injection, which involves transferring the animal to the imaging bed and setting the parameters, such as scan range, in the operating software before initiating the CT scan. Therefore, there is an urgent need to develop a vascular contrast medium for CT which is inexpensive and well-excreted after relatively prolonged in vivo circulation without the need for high-dose amount, not only for the diagnosis of cardiovascular diseases requiring high-dose amount, but also for the micro-CT experiments using small animals.

For this purpose, papers and patents related to CT contrast media containing iodine using dendrimers as macromolecular scaffolds started to appear around 1990. That is, if a monomolecular dendrimer is used as a macromolecular scaffold (see descriptions below), the reproducibility in terms of both the preparation and effects can be achieved. Also, the facile excretion after certain period of intravascular circulation is expected, because the size of the dendrimers is much smaller than that of the contrast agents based on metal nanoparticles or self-assembly of linear polymers.

The dendrimer is a relatively small treelike (or radial-shaped) macromolecule of generally 10 nm or less in diameter, and is a pure molecule with a single molecular weight value made by stepwise (i.e., adding one layer) iterative organic synthesis and purification. Unlike most of other traditional macromolecules (polydispersed mixtures), dendrimers have predictable size in a specific environment (solvent, pH, temperature, etc.) and thus are advantageous for the applications which require the use of macromolecules of specific hydrodynamic diameters. Some advantages of dendrimers include structural integrity, unlimited possibility to vary the component functional groups by organic synthesis and the corresponding physicochemical properties, feasibility to covalently attach various functional units (e.g., small molecular drugs, targeting agents, surface modifiers, etc.) to the interior and the surface of the dendrimers, and very low enzymatic degradation rate which is important for biological applications.

Examples of using dendrimers for biomedical applications include, gene transfection by forming charge complex between the polycationic dendrimers and anionic genes; drug delivery where the drugs were either encapsulated in the interior void of the dendrimers or covalently attached to the dendrimers so they can be released by a specific stimulus (pH, light, enzyme, etc.) at the disease sites; targeted delivery or controlled release of drugs by modifying the structures of carrier dendrimers; multivalent effects through which the binding affinity between the carbohydrate ligands and lectins at the extracellular membrane can be enhanced significantly; medical diagnosis for the signal amplification of imaging agents by substituting multiple copies of small molecular imaging agents at the dendrimer scaffold; tissue engineering using biocompatible and biodegradable dendrimers.

Since the advent of the first dendrimer in the late 1970s by Denkewalter as a polylysine dendrimer, the research focus on the dendrimer field has shifted from the molecular design of new dendrimers and development of their synthetic methodologies to the investigation of the physicochemical properties of various types of dendrimers and some basic applications utilizing their specific properties (e.g., self-assembly, biomimetic systems, etc.), and more recently, to the advanced applications of dendrimers for materials science and biomedicine. An example of the structure of the polylysine dendrimer synthesized by Denkewalter is shown below (Patent Literature 2 [U.S. Pat. No. 4,410,688]).

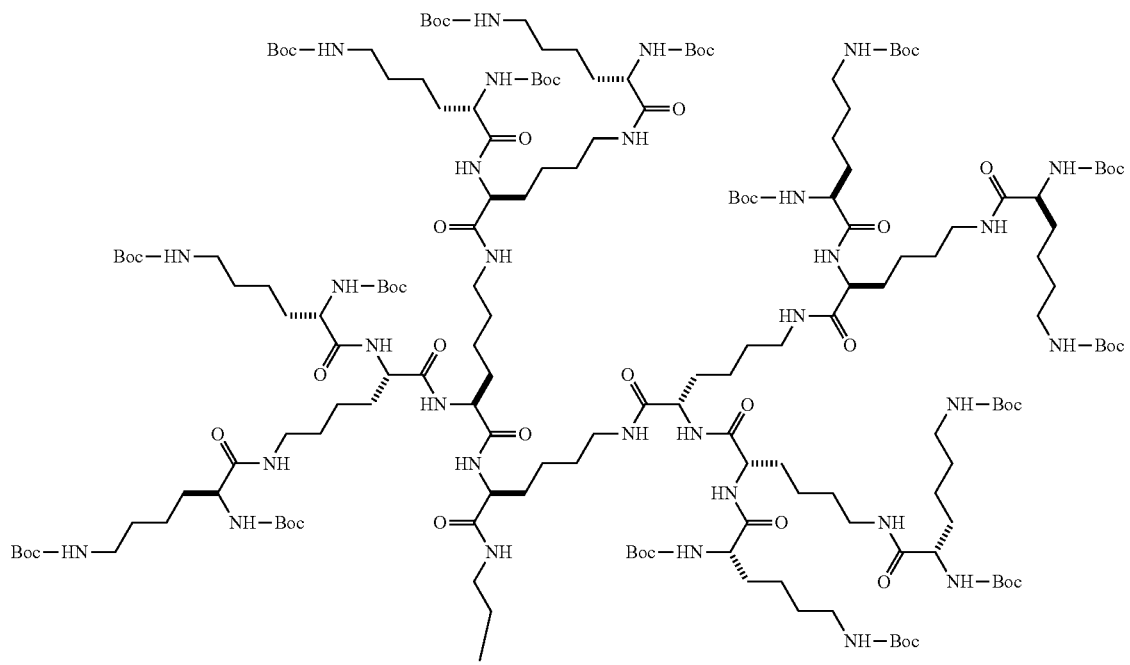

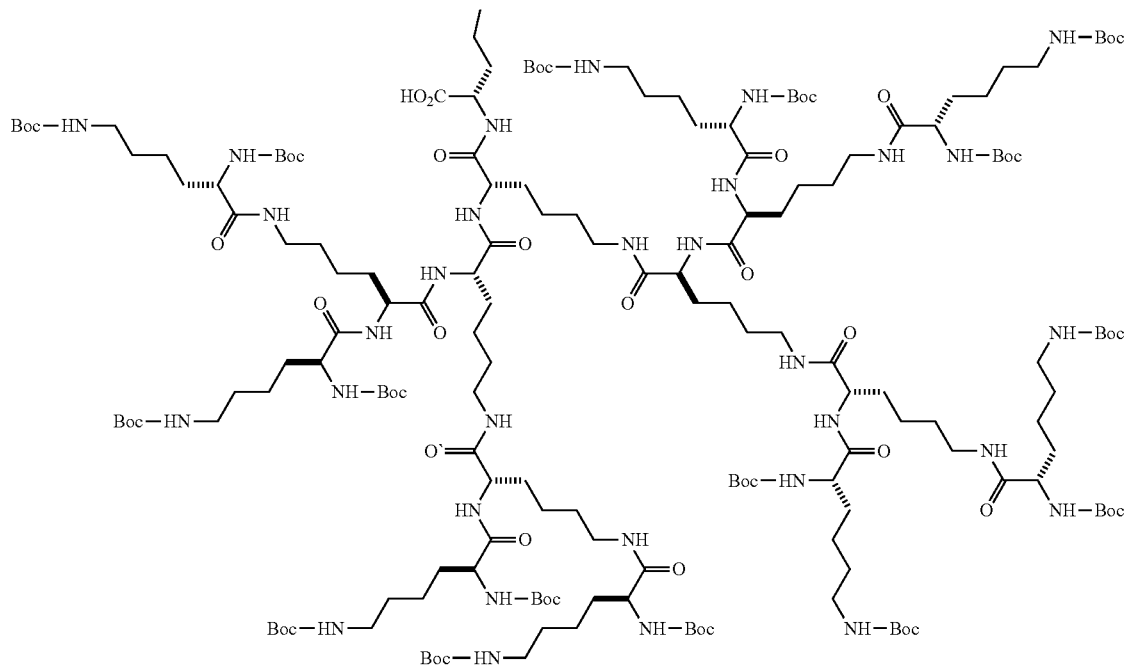

Also, the poly(amidoamine) (PAMAM) dendrimer was developed by Dr. Donald A. Tomalia in the 1980s while he was working at the Dow Chemical company. The interior of PAMAM dendrimer is composed of aliphatic amino and amide groups and the surface groups can be amine, carboxylate, hydroxyl, and so on. For example, the structures of the first, second, third, and fourth generation (G1, G2, G3, and G4) PAMAM dendrimers with ethylenediamine as a core unit and the amine as the surface group are shown below.

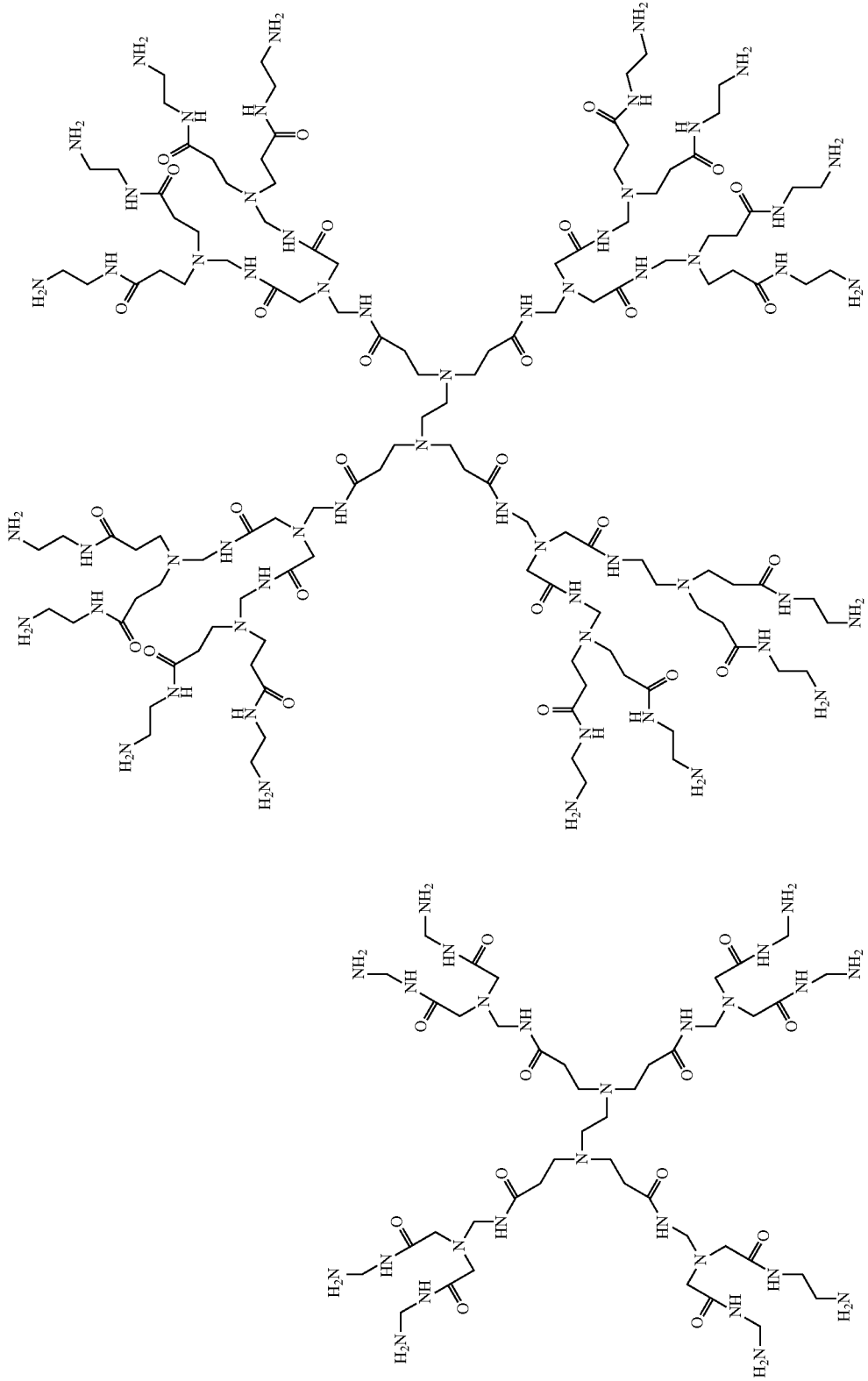

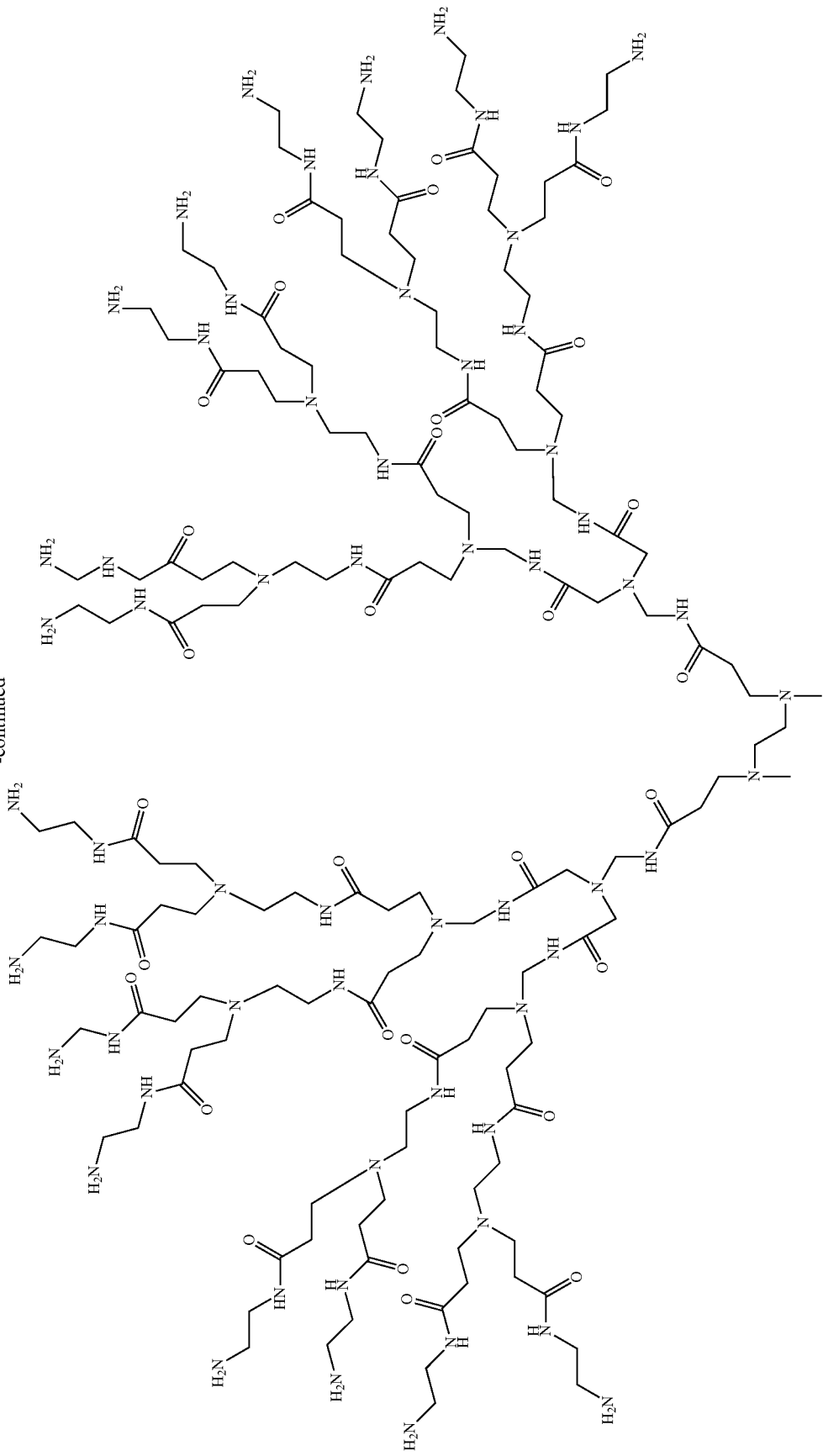
-continued

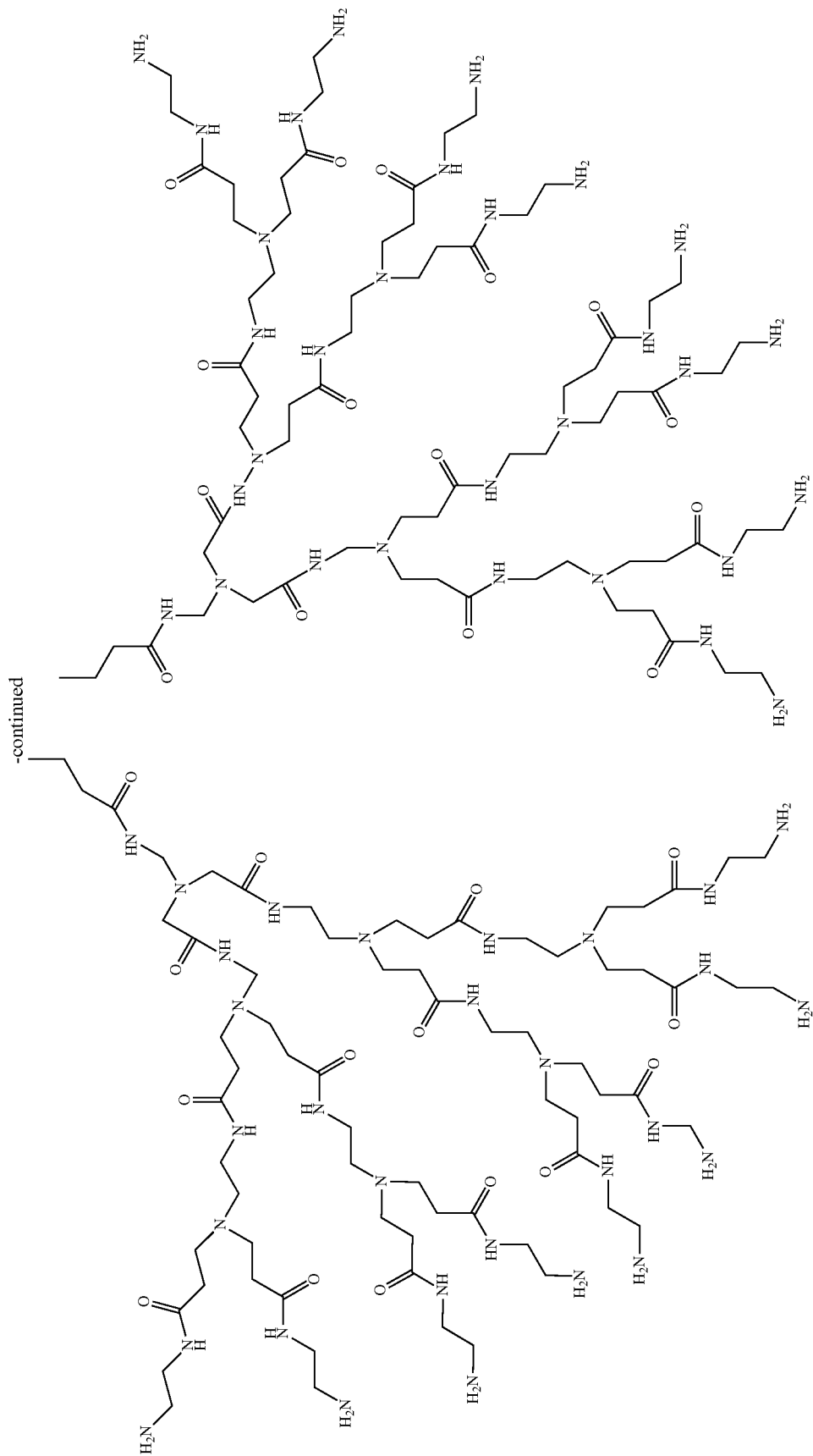

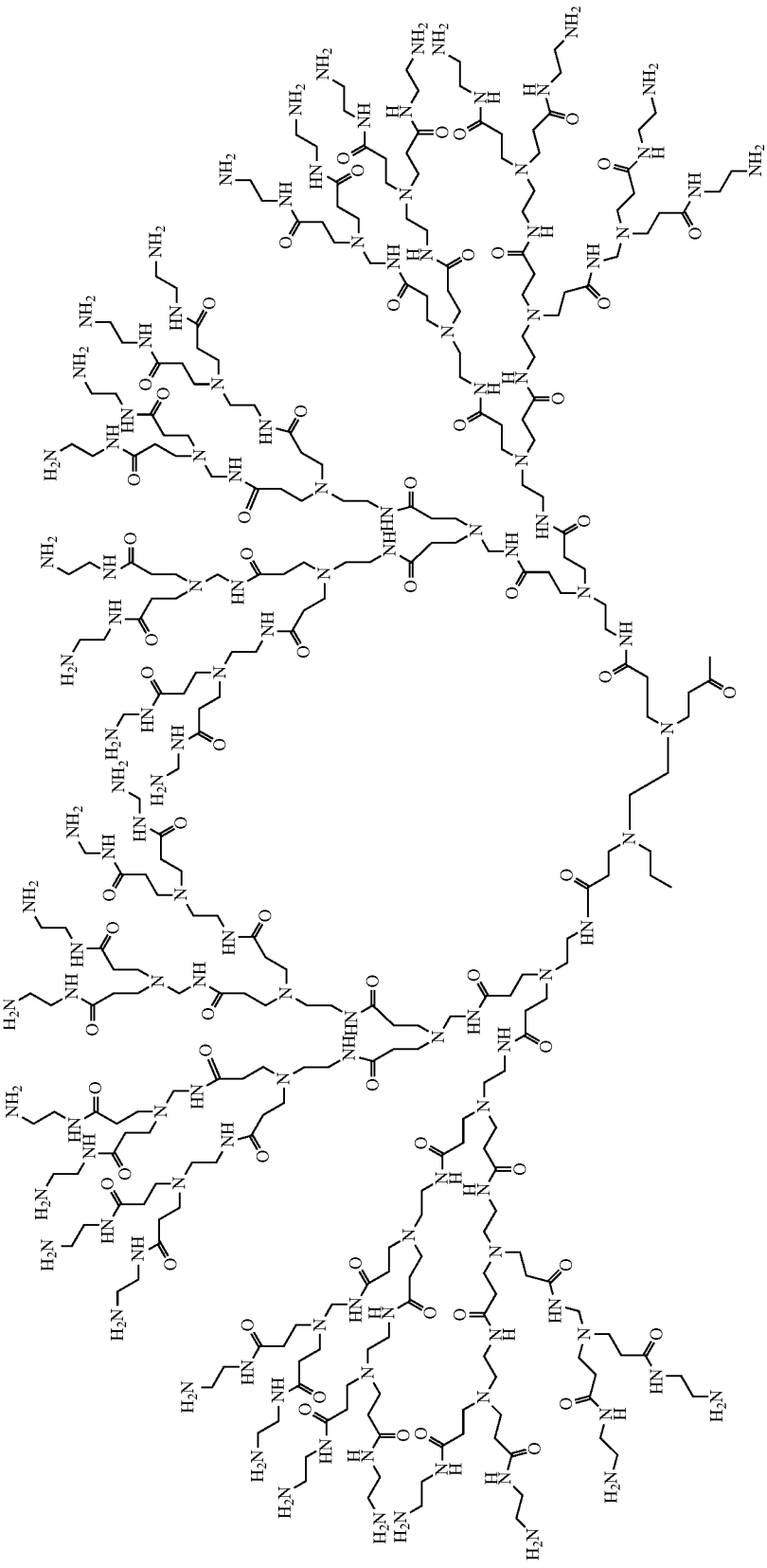

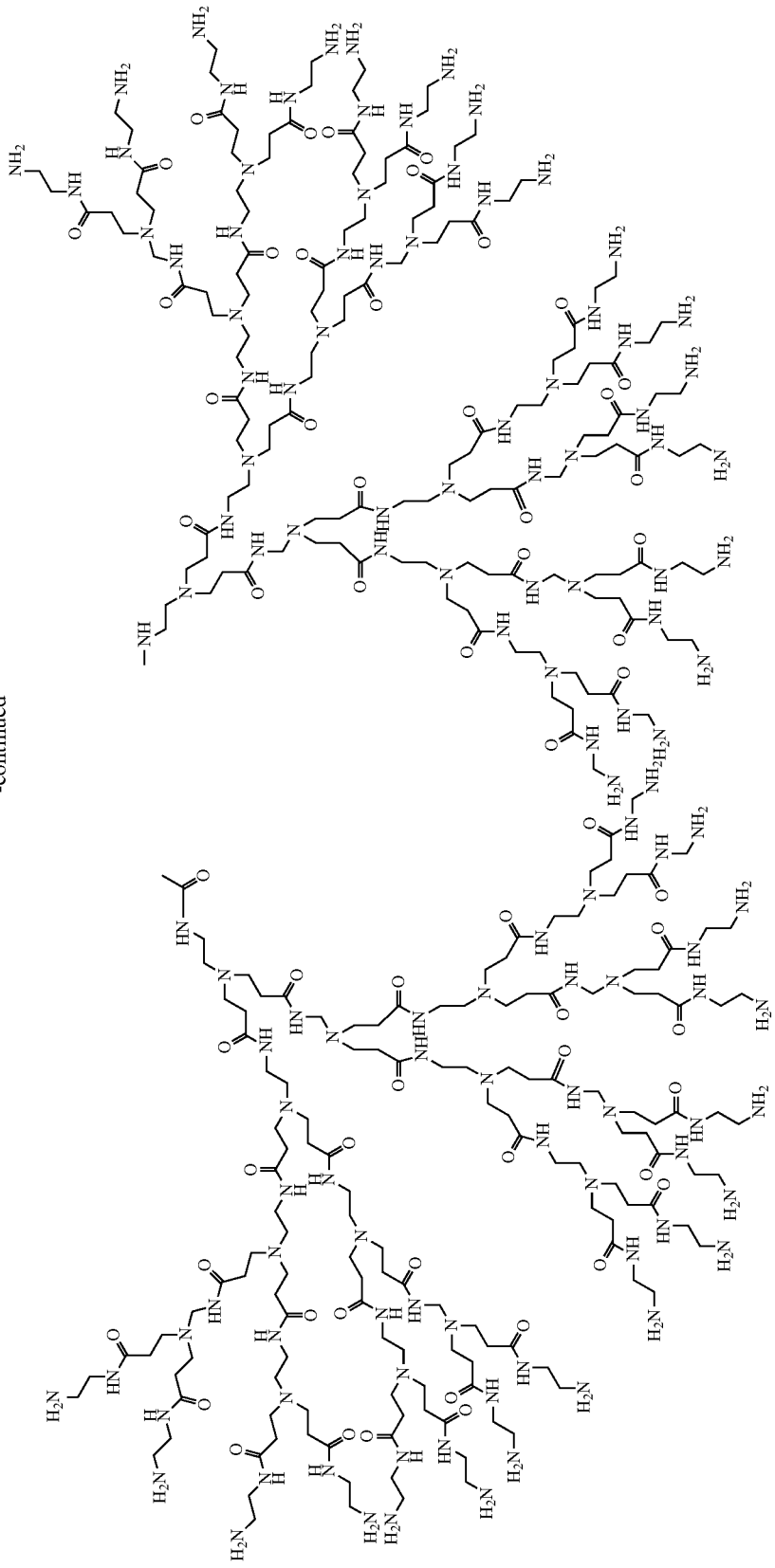
G4 PAMAM Dendrimer (4a)

PAMAM dendrimers are popular for in vivo applications among several commercially available dendrimers, and have been widely used for various biomedical applications. While the dendrimers made by stepwise organic synthesis and purification are, in principle, monomolecular with single molecular weight values, these commercially available PAMAM dendrimers (manufactured by Dendritech, Inc., sold by Sigma-Aldrich Corporation) contain structural defects and are heterogeneous (polydispersity index (PDI), ca. 1.01-1.1) with some unwanted side-products because they were synthesized through a divergent approach where the excess amount of reagents were added for reactions and the purification was done roughly for large-scale production. Thus, the structural analysis of PAMAM dendrimers or their derivatives at the monomolecular level with a single molecular weight is not possible. However, it would be reasonable to use PAMAM dendrimers in order to quickly examine the potential of adopting dendrimers for specific biological applications before designing and synthesizing an optimal biocompatible dendrimer with a single molecular weight value.

Not many examples of dendrimer-based CT contrast media containing iodine have been reported to date. This could be due to the complex preparation methods involving many synthetic steps, relatively high toxicity, minor degree of extension of the duration of contrast enhancement compared to that of small molecular contrast agents containing iodine, and relatively poor image quality (i.e., contrast enhancement) (Non-Patent Literature 10 [W. Krause, et al., Top. Curr. Chem. 2000, 210, 261-308], Patent Literature 3 [PCT/EP94/04245], Patent Literature 4 [PCT/EP96/02450], Patent Literature 5 [PCT/FR92/01135], Patent Literature 6 [PCT/EP94/648203], Patent Literature 7 [PCT/EP95/730573], Patent Literature 8 [PCT/EP95/78263], Non-Patent Literature 11 [A. T. Yordanov, et al., Nano Lett. 2002, 2, 595-599], and Non-Patent Literature 12 [Y. Fu, et al., Bioconjugate Chem. 2006, 17, 1043-1056]).

Meanwhile, a greater amount of research has been conducted on the dendrimer-based MRI contrast media, for example, Bayer Schering Pharma AG. who developed gadopentetate dimeglumine (Gd-DTPA, brand name: Magnevist), a representative small molecular vascular contrast medium for MRI currently administered to patients in the hospital, has developed the dendrimer-based vascular contrast medium for MRI (EP 430863, WO 97/02051, WO 98/24775, WO 98/24774, and U.S. Pat. No. 5,911,971), and the clinical trials for "Gadomer-17" (or referred to as "Gd-DTPA-17" or "SH L643 A"; K. Nael, et al., J. Magn. Reson. Imaging 2007, 25, 66-72; B. Misselwitz, et al., Magn. Reson. Mater. Phys. Biol. Med. 2001, 12, 128-134) are underway.

Therefore, there is a current need to develop a CT contrast medium including iodine-containing radial-shaped macromolecules with excellent contrast enhancement, which can overcome the current limitations of the small molecular CT contrast agents containing iodine used in clinic. Ideally, this CT contrast medium should be made by relatively simple synthetic methods, be inexpensive, have prolonged intravascular circulation time sufficient for the diagnosis of cardiovascular diseases, and be mostly excreted through a safe route at the adequate time point after the administration.

Accordingly, while conducting research on the CT contrast medium that can overcome foregoing limitations, the present inventors confirmed that by using the iodine-containing radial-shaped macromolecules featuring a protective layer made of biocompatible polymers which surrounds the iodine-containing compounds substituted in the core or the interior region, the duration of contrast enhancement has been significantly improved in comparison to that of the current small molecular contrast media compounds containing iodine, the in vivo toxicity has been reduced by forming a protective layer with relatively long biocompatible polymer chains which prevents the exposure of the toxic iodine-containing compounds substituted near the surface of the core region to the external environment for potential adverse effects, the in vivo circulation time has been increased by preventing rapid uptake by macrophages, the excretion has been realized at the adequate time point after the intravascular injection, the large-scale production at high yield and low cost is amenable due to the simple preparation and purification methods, the reproducibility in terms of the preparation and effects is high due to the relatively low polydispersity, and the structural integrity of the iodine-containing radial-shaped macromolecules is ensured because the compound is entirely formed by covalent binds, thereby leading to the completion of the present invention.

SUMMARY OF THE INVENTION

One object of the present invention is to provide an iodine-containing radial-shaped macromolecule.

Another object of the present invention is to provide a method of preparing the iodine-containing radial-shaped macromolecule.

Still another object of the present invention is to provide a composition for a computed tomography (CT) contrast medium which includes the iodine-containing radial-shaped macromolecule.

In order to achieve the objects, the present invention provides an iodine-containing radial-shaped macromolecule including: a core composed of a circular or spherical symmetric small molecular compound, or a radial-shaped macromolecule; an iodine-containing compound bound to the core directly or through a peptide; and a biocompatible polymer bound to the core directly or through a peptide, or directly bound to the iodine-containing compound bound to the core, wherein the iodine-containing radial-shaped macromolecule has a structure in which the biocompatible polymers form a protective layer to prevent the exposure of the core and the iodine-containing compound in vivo.

The present invention also provides a method of preparing the iodine-containing radial-shaped macromolecule including: binding the biocompatible polymer to a portion of the surface functional groups of the core composed of a circular or spherical symmetric small molecular compound, or a radial-shaped macromolecule (step 1); and binding the iodine-containing compound to the unreacted surface functional groups of the core in step 1 directly or through a peptide (step 2).

Furthermore, the present invention provides a method of preparing the iodine-containing radial-shaped macromolecule including: binding the iodine-containing compound to a portion of the surface functional groups of the core composed of a circular or spherical symmetric small molecular compound, or a radial-shaped macromolecule (step 1); and binding the biocompatible polymer to the iodine-containing compound attached to the core in step 1 (step 2).

The present invention also provides a method of preparing the iodine-containing radial-shaped macromolecule including: binding the iodine-containing compound to a biocompatible polymer through a peptide (step 1); and binding the iodine-containing compound bound to the biocompatible polymer through the peptide in step 1 to the surface functional groups of the core composed of a circular or spherical symmetric small molecular compound, or a radial-shaped macromolecule (step 2).

Furthermore, the present invention provides a CT contrast medium composition comprising the iodine-containing radial-shaped macromolecule as an active ingredient.

With respect to the iodine-containing radial-shaped macromolecule according to the present invention, the duration of contrast enhancement has been significantly improved in comparison to that of the current small molecular contrast media compounds containing iodine, the in vivo toxicity has been reduced by forming a protective layer with relatively long biocompatible polymer chains which prevents the exposure of the toxic iodine-containing compounds substituted near the surface of the core region to the external environment for potential adverse effects, the in vivo circulation time has been increased by preventing rapid uptake by macrophages, the excretion has been realized at the adequate time point after the intravascular injection, the large-scale production at high yield and low cost is amenable due to the simple preparation and purification methods, the reproducibility in terms of the preparation and effects is high due to the relatively low polydispersity, and the structural integrity of the iodine-containing radial-shaped macromolecules is ensured because the compound is entirely formed by covalent binds. Therefore, the iodine-containing radial-shaped macromolecule may be suitable for the preparation of a CT contrast medium.

BRIEF DESCRIPTION OF THE DRAWINGS

The above and other objects, features, and other advantages of the present invention will be more clearly understood from the following detailed description taken in conjunction with the accompanying drawings, in which.

DESCRIPTION OF THE PREFERRED EMBODIMENTS

Figure 1:
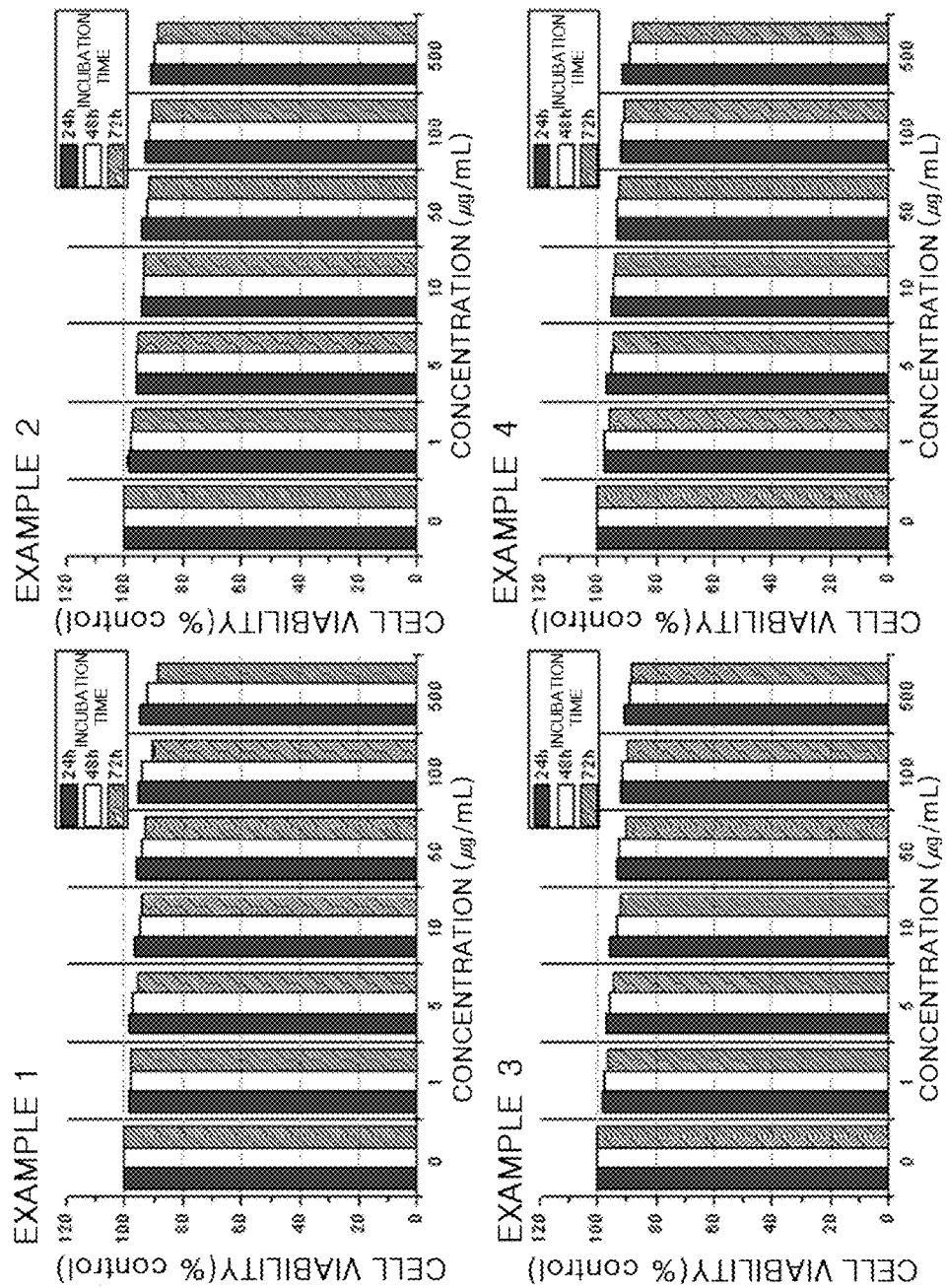
FIG. 1 illustrates a graph in which cytotoxicity is measured using the compounds according to the embodiment of the present invention (a: Example 1; b: Example 2; c: Example 3; d: Example 4)

Features and advantages of the present invention will be more clearly understood by the following detailed description of the present preferred embodiments by reference to the accompanying drawings. First, it should be noted that the terms or words used herein should be construed as meanings or concepts corresponding to the technical spirit of the present invention, based on the principle that the inventor can appropriately define the concepts of the terms to best describe his or her own invention. Also, it should be understood that the detailed descriptions of well-known functions and structures related to the present invention will be omitted so as not to unnecessarily obscure the important points of the present invention.

Hereinafter, the present invention will be described in detail.

The present invention provides an iodine-containing radial-shaped macromolecule including:

a core composed of a circular or spherical symmetric small molecular compound, or a radial-shaped macromolecule;

an iodine-containing compound bound to the core directly or through a peptide; and a biocompatible polymer bound to the core directly or through a peptide, or directly bound to the iodine-containing compound bound to the core, wherein the iodine-containing radial-shaped macromolecule has a structure in which the biocompatible polymers form a protective layer to prevent the exposure of the core and the iodine-containing compound in vivo.

In the iodine-containing radial-shaped macromolecule according to the present invention, any one of the carbohydrates selected from the group consisting of α-, β-, and γ-cyclodextrin, glucose, galactose, mannose, and derivatives thereof, porphyrin and derivatives thereof, 1,4,7,10-tetraazacyclododecane-1,4,7,10-tetraacetic acid (DOTA) and derivatives thereof, a cyclic peptide formed by connecting two to four peptides selected from the group consisting of lysine, aspartic acid, glutamic acid, serine, cysteine, and tyrosine, and derivatives thereof may be used as the circular or spherical symmetric small molecular compound constituting the core.

Any one of the dendrimers selected from the group consisting of a poly(amidoamine) (PAMAM) dendrimer, a polylysine dendrimer, a poly(propylene imine) (PPI) dendrimer, a polyester dendrimer, a polyglutamic acid dendrimer, a polyaspartic acid dendrimer, a polyglycerol dendrimer, and a polymelamine dendrimer, any one of the hyperbranched polymers selected from the group consisting of polylysine, polyester, polyglutamic acid, polyaspartic acid, and polyglycerol, any one of the star-shaped polymers selected from the group consisting of polyethylene glycol (PEG) and copolymer derivatives thereof, and derivatives thereof may be used as the radial-shaped macromolecule constituting the core.

In the iodine-containing radial-shaped macromolecule according to the present invention, compounds represented as the following Chemical Formulae 2, 3, 4, and 10 may be used as preferred examples of the iodine-containing compound.

[Chemical Formula 2]

[Chemical Formula 3]

[Chemical Formula 4]

[Chemical Formula 10]

Regarding Chemical Formulae 2 to 4 or Chemical Formula 10, $R^1$, $R^2$, and $R^3$ are each independently or selectively —$NH_2$, —$NHR^4$, —$NR^4{}_2$, —$NHNH_2$, —$NHNHR^4$, —$NHNR^4{}_2$, —OH, —$OR^4$, —SH, or —$SR^4$, $R^4$ is —H, -Boc, an unsubstituted or substituted straight or branched $C_{1-6}$ alkyl or heteroalkyl, or an unsubstituted or substituted $C_{5-7}$ aryl or heteroaryl, and $R^5$ is the same as $R^4$ or —(C=O)$R^4$, —(C=O)$OR^4$, —(C=O)$NHR^4$, or —(C=O)$NR^4{}_2$.

Here, the iodine-containing compounds of Chemical Formulae 2, 3, and 4 may be prepared by using iodine compounds represented as the following Chemical Formula 1 or Chemical Formula 9 as a precursor.

[Chemical Formula 1]

[Chemical Formula 9]

In the iodine-containing radial-shaped macromolecule according to the present invention, PEG, hyaluronic acid, heparin, and a derivative thereof may be used as the biocompatible polymer.

In the iodine-containing radial-shaped macromolecule according to the present invention, the peptide is composed of 2 to 4 amino acid repeat units and may be selected from the group consisting of dilysine, trilysine, tetralysine, diglutamic acid, triglutamic acid, tetraglutamic acid, diaspartic acid, triaspartic acid, tetraaspartic acid, dicysteine, tricysteine, tetracysteine, diserine, triserine, and tetraserine.

In the iodine-containing radial-shaped macromolecule according to the present invention, in the case that the core, the iodine-containing compound, the peptide, or the biocompatible polymer are covalently linked to one another, the linkages may be —NHC(=O)—, —C(=O)O—, —NHC(=O)NH—, —NHC(=O)O—, —NHC(=S)NH—, —C=N—NH—, —C=N—NHC(=O)—, —NH—, —S—, —SS—, —$NHCH_2CH(OH)$—, —O—, or Furthermore, both ends of the linkages may be each bound to the core, the iodine-containing compound, the peptide, or the biocompatible polymer additionally through any one selected independently or selectively from the group consisting of —$(CH_2)_m$—, —$(CH_2)_m(C=O)$—, $C_{3-20}$ cycloalkyl-$(CH_2)_m$—, $C_{4-20}$ aryl-$(CH_2)_m$—, and —NH—$CH_2CH_2$—, where m is an integer between 0 and 10.

In the iodine-containing radial-shaped macromolecule according to the present invention, the core has one or more surface functional groups selected form the group consisting of amine, hydroxyl, hydroxylamine, carboxyl, carboxyhydrazide, hydrazine, thiol, azide, alkynyl, halogen, aldehyde, ketone, epoxy, 3-carbomethoxypyrrolidinone, and tri-($C_{1-4}$ alkoxy)-silyl, which can be covalently linked to the iodine-containing compound, the peptide, or the biocompatible polymer.

The preferred average molecular weight of the iodine-containing radial-shaped macromolecule according to the present invention is in the range of 8,000 Da to 150,000 Da. If the average molecular weight is lower than 8,000 Da, prolonged intravascular circulation may not be achieved and the iodine-containing radial-shaped macromolecule may be relatively rapidly discharged through kidney similar to the small molecular compounds. If the average molecular weight is higher than 150,000 Da, there may be problems such as difficulties in the intravascular injection due to high viscosity, high risk of adverse effects (shock, allergy, etc.), increased accumulation in the liver due to high toxicity, and difficulties in excretion (relatively long half-life).

The theoretical average molecular weights based on the analyses of integration values in the $^1$H nuclear magnetic resonance (NMR) spectra and iodine contents determined by the inductively coupled plasma mass spectrometry (ICP-MS) of the macromolecules 1c, 2c, 3c, and 4c made from G1, G2, G3, and G4 PAMAM dendrimers, respectively, as cores in Examples 1 to 4 of the present invention are about 10,000 Da, 18,000 Da, 40,000 Da, and 86,000 Da, respectively. Therefore, it is reasonable to select the preferred average molecular weight to be in a range of 8,000 Da to 150,000 Da considering that the final compounds contain polydisperse PAMAM dendrimers and PEG chains.

Figure 3:
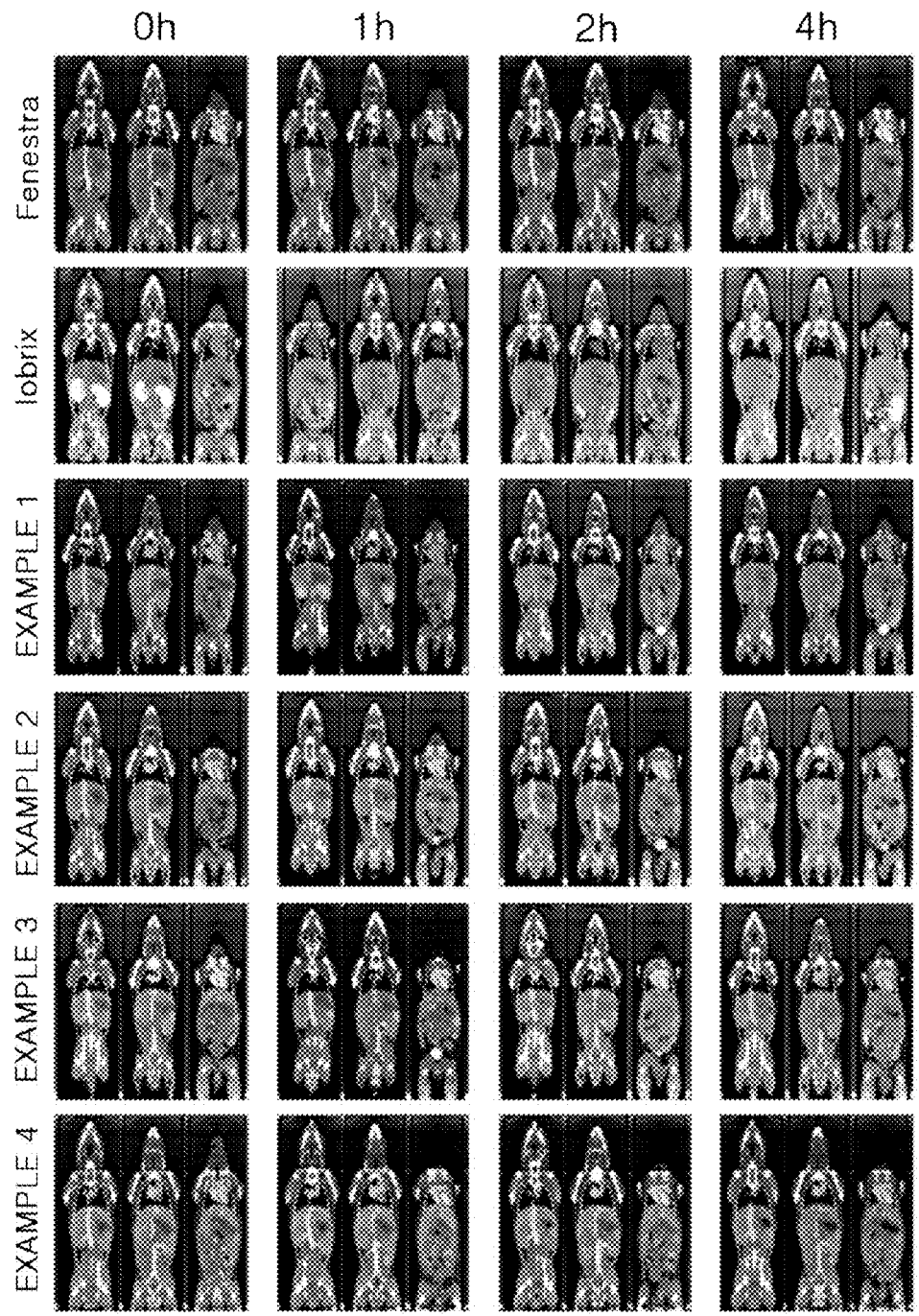
FIG. 3 illustrates the whole-body coronal CT images of mice administered with the CT contrast media containing the compounds according to the embodiment of the present invention obtained using micro-CT at the selected time points of 0, 1, 2, and 4 hours post-injection.

For reference, for Compound 1c of Example 1 having the lowest molecular weight among Examples, a considerable amount thereof was found in the kidney within a relatively short period of time (see the images taken at 1 hour elapsed) after injection of a contrast medium as illustrated in FIG. 3. For Compound 4c of Example 4 having the highest molecular weight, a contrast medium solution thereof felt thicker than Compound 2c of Example 2 or Compound 3c of Example 3 during the injection, and it was more difficult to dissolve Compound 4c in a buffer solution than Compounds 1c, 2c, or 3c requiring longer period of sonication with relatively more heat evolved. Therefore, it is considered that it is not appropriate to prepare a compound with the molecular weight higher than that of Compound 4c as a CT contrast medium by using a method similar to that of the present invention.

In fact, a contrast medium based on the G5 PAMAM dendrimer was prepared, and the synthesis and characterization were completed. However, it was not possible to use this compound for the actual intravascular injection experiments because it was difficult to dissolve the compound in a buffer solution at the concentration appropriate for CT imaging. Also, the compound thereof was considered to be not so useful because of its heterogeneity with relatively high polydispersity index (PDI).

Compounds represented as the following Chemical Formulae 5 to 8 may be used as preferred examples of the iodine-containing radial-shaped macromolecule according to the present invention.

[Chemical Formula 5]

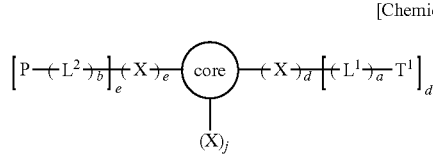

[Chemical Formula 6]

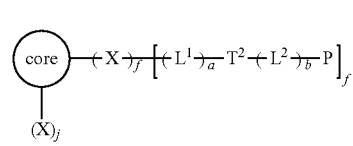

[Chemical Formula 7]

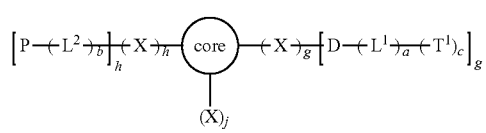

[Chemical Formula 8]

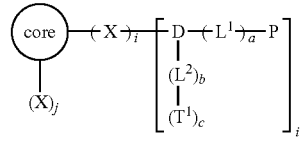

Regarding Chemical Formulae 5 to 8, the core is any one of carbohydrates selected from the group consisting of α-, β-, and γ-cyclodextrin, glucose, galactose, and mannose, and derivatives thereof, porphyrin and derivatives thereof, 1,4,7,10-tetraazacyclododecane-1,4,7,10-tetraacetic acid (DOTA) and derivatives thereof, a cyclic peptide formed by connecting two to four peptides selected from the group consisting of lysine, aspartic acid, glutamic acid, serine, cysteine, and tyrosine, and derivatives thereof, any one of dendrimers selected from the group consisting of a poly(amidoamine) (PAMAM) dendrimer, a polylysine dendrimer, a poly(propylene imine) (PPI) dendrimer, a polyester dendrimer, a polyglutamic acid dendrimer, a polyaspartic acid dendrimer, a polyglycerol dendrimer, and a polymelamine dendrimer, any one of hyperbranched polymers selected from the group consisting of polylysine, polyester, polyglutamic acid, polyaspartic acid, and polyglycerol, any one of the star-shaped polymers selected from the group consisting of polyethylene glycol (PEG) and copolymer derivatives thereof, and derivatives thereof, $T^1$ and $T^2$ are iodine-containing compounds, in which $T^1$ is

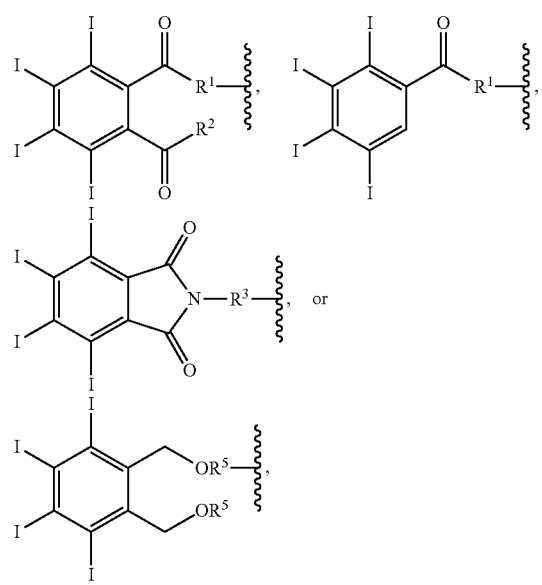

and $T^2$ is

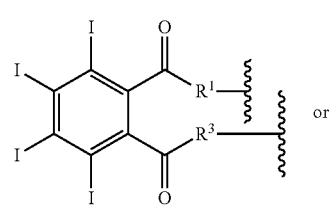

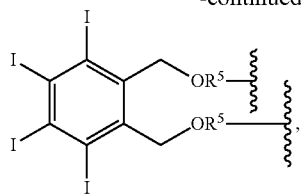

wherein $R^1$ and $R^3$ are each independently or selectively —NH—, —NR$^4$—, —NNH$_2$—, —NNHR$^4$—, —NNR$^4{}_2$—, —O—, or —S—, $R^2$ is —NH$_2$, —NHR$^4$, —NR$^4{}_2$, —NHNH$_2$, —NHNHR$^4$, —NHNR$^4{}_2$, —OH, —OR$^4$, —SH, or —SR$^4$, $R^4$ is —H, -Boc, a straight or branched $C_{1-6}$ alkyl, or an unsubstituted or substituted $C_{5-7}$ aryl or heteroaryl, and $R^5$ is the same as $R^4$ or —(C=O)R$^4$, —(C=O)OR$^4$, —(C=O)NHR$^4$, or —(C=O)NR$^4{}_2$, D is a peptide composed of 2 to 4 amino acid repeat units and may be selected from the group consisting of dilysine, trilysine, tetralysine, diglutamic acid, triglutamic acid, tetraglutamic acid, diaspartic acid, triaspartic acid, tetraaspartic acid, dicysteine, tricysteine, tetracysteine, diserine, triserine, and tetraserine, P is PEG, hyaluronic acid, heparin, and derivatives thereof, X is a surface functional group of the core and may be amine, hydroxyl, hydroxylamine, carboxyl, carboxyhydrazide, hydrazine, thiol, azide, alkynyl, halogen, aldehyde, ketone, epoxy, 3-carbomethoxypyrrolidinone, and tri-($C_{1-4}$ alkoxy)-silyl, $L^1$ and $L^2$ are linkages between the core, the iodine-containing compound ($T^1$ or $T^2$), the peptide (D), or the biocompatible polymer (P), and may be —NHC(=O)—, —C(=O)O—, —NHC(=O)NH—, —NHC(=O)O—, —NHC(=S)NH—, —C=N—NH—, —C=N—NHC(=O)—, —NH—, —S—, —SS—, —NHCH$_2$CH(OH)—, —O—, or

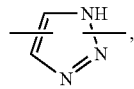

and both ends of the linkages are each bound to the core, the iodine-containing compound, the peptide, or the biocompatible polymer additionally through any one selected independently or selectively from the group consisting of —(CH$_2$)$_m$—, —(CH$_2$)$_m$(C=O)—, $C_{3-20}$ cycloalkyl-(CH$_2$)$_m$—, $C_{4-20}$ aryl-(CH$_2$)$_m$—, and —NH—CH$_2$CH$_2$—, wherein m is an integer between 0 and 10, a and b are each independently or selectively an integer of 0 or 1, c is an integer between 2 and 4, d, e, f, g, h, and i are each independently or selectively an integer between 2 and 60, and j is an integer between 1 and 10.

Here, regarding Chemical Formulae 7 and 8, in the case that the biocompatible polymer is PEG, it is preferred to use a $C_{1-4}$ alkoxy group as the end group for PEG, where the end group is located toward the outside from the core.

In order to describe specifically the compounds represented as Chemical Formulae 5 to 8 as preferred examples of the iodine-containing radial-shaped macromolecule according to the present invention, schematic images thereof are presented below.

A

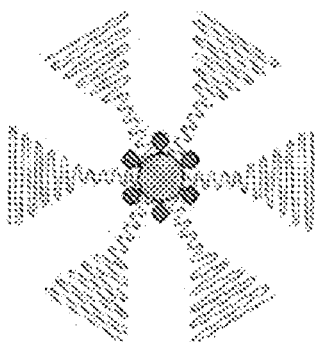

B

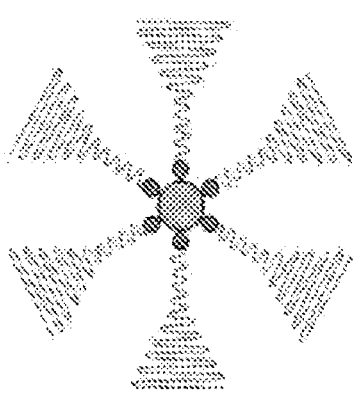

C

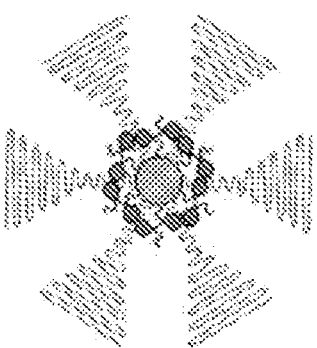

D

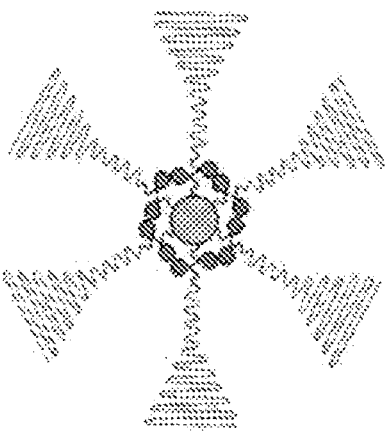

In the mages foregoing, with respect to A, the compound of Chemical Formula 5 is presented where the iodine-containing compounds (the small red circles) and biocompatible polymers (the long green wavy lines) are independently bound to the core (the large gray circle), with respect to B, the compound of Chemical Formula 6 is presented where the biocompatible polymers are bound to the iodine-containing compounds bound to the core, with respect to C, the compound of Chemical Formula 7 is presented where the biocompatible polymers and the peptides (the short blue wavy lines) with 2 to 4 units of iodine-containing compounds substituted are independently bound to the core, and with respect to D, the compound of Chemical Formula 8 is presented where the biocompatible polymers are bound to the core-bound peptides with 2 to 4 units of iodine-containing compounds substituted.

With respect to the iodine-containing radial-shaped macromolecule according to the present invention, the duration of contrast enhancement has been significantly improved in comparison to that of the current small molecular contrast media compounds containing iodine, the in vivo toxicity has been reduced by forming a protective layer with relatively long biocompatible polymer chains which prevents the exposure of the toxic iodine-containing compounds substituted near the surface of the core region to the external environment for potential adverse effects, the in vivo circulation time has been increased by preventing rapid uptake by macrophages, the excretion has been realized at the adequate time point after the intravascular injection, the large-scale production at high yield and low cost is amenable due to the simple preparation and purification methods, the reproducibility in terms of the preparation and effects is high due to the relatively low polydispersity, and the structural integrity of the iodine-containing radial-shaped macromolecules is ensured because the compound is entirely formed by covalent binds. Therefore, the iodine-containing radial-shaped macromolecule may be suitable for the preparation of a CT contrast medium.

Also, the present invention provides a method of preparing the iodine-containing radial-shaped macromolecule including:

binding the biocompatible polymer to a portion of the surface functional groups of the core composed of a circular or spherical symmetric small molecular compound, or a radial-shaped macromolecule (step 1); and binding the iodine-containing compound to the unreacted surface functional groups of the core in step 1 directly or through a peptide (step 2).

Furthermore, the present invention provides a method of preparing the iodine-containing radial-shaped macromolecule including:

binding the iodine-containing compound to a portion of the surface functional groups of the core composed of a circular or spherical symmetric small molecular compound, or a radial-shaped macromolecule (step 1); and binding the biocompatible polymer to the iodine-containing compound attached to the core in step 1 (step 2).

The present invention also provides a method of preparing the iodine-containing radial-shaped macromolecule including:

binding the iodine-containing compound to a biocompatible polymer through a peptide (step 1); and binding the iodine-containing compound bound to the biocompatible polymer through the peptide in step 1 to the surface functional groups of the core composed of a circular or spherical symmetric small molecular compound, or a radial-shaped macromolecule (step 2).

In the methods of preparing the iodine-containing radial-shaped macromolecule according to the present invention, examples of the circular or spherical symmetric small molecular compound, the radial-shaped macromolecule, the surface functional group, the iodine-containing compound, the peptide, and the biocompatible polymer are the same as described above.

In the preparation method according to the embodiment of the present invention, about 15% to 50% of the surface functional groups of the core are derivatized with the biocompatible polymer, and then the excessive amount of the iodine-containing compound is treated to react with the remaining functional groups of the core. Thereby, the iodine content of the radial-shaped macromolecule may be controlled to be in the range of about 15% to 50%.

Also, the present invention provides a CT contrast medium composition containing the iodine-containing radial-shaped macromolecule as an active ingredient.

Here, the preferred iodine content of the iodine-containing radial-shaped macromolecule may be in the range of 15% to 50%. If the iodine content of the iodine-containing radial-shaped macromolecule is lower than 15%, possibility to induce adverse effects during the intravascular injection is high because an excessive amount of the contrast medium must be administered in order to achieve a proper level of contrast enhancement. If the iodine content of the iodine-containing radial-shaped macromolecule is higher than 50%, the contrast medium may not be suitable for in vivo applications due to high toxicity.

Hereinafter, examples and experimental examples of the preferred embodiments of the present invention are provided in order to aid in understanding. However, the following examples and experimental examples are provided for illustrative purposes only, and the scope of the present invention should not be limited thereto in any manner.

Preparational Example 1

Preparation of Cyclized Neutral Phthalimide Derivative (8)

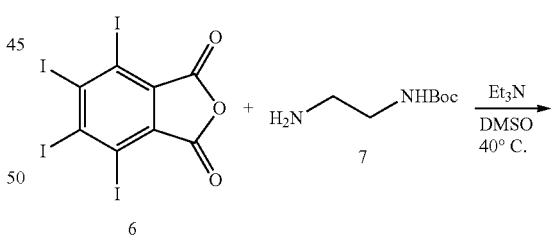

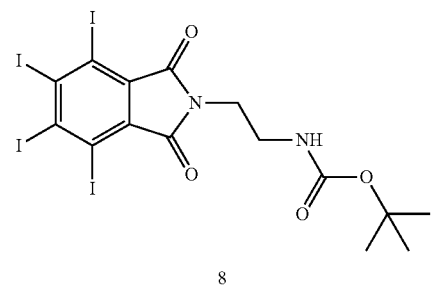

To a solution of Compound 6 (4,5,6,7-tetraiodobenzofuran-1,3-dione (TIPN), 2.40 g, 3.68 mmol) and Compound 7 (N-tert-Boc-ethylenediamine, 200 mg, 1.22 mmol) in dimethyl sulfoxide (DMSO) (5 mL) was added triethylamine (0.50 mL, 3.59 mmol). The reaction was heated at 40° C. and stirred for 16 hours under a dry argon atmosphere. The reaction mixture was passed through a size-exclusion chromatography (SEC) column (model: Bio-Beads S-X1, H 36 cm×O.D. 4.5 cm, manufacturer: Bio-Rad) in N,N-dimethylformamide (DMF) to remove DMSO, concentrated under reduced pressure, and the crude product was chromatographed on silica gel (20:1 methylene chloride (CH$_2$Cl$_2$)/acetone) to give 60.1 mg of Compound 8 (75.7 mol, 6%) as a yellow powder.

R$_f$: 0.63 [silica gel, 10:1 CH$_2$Cl$_2$/acetone];
$^1$H NMR (600 MHz, DMSO-d$_6$) δ 6.89 (t, 1H, J=6.4 Hz, H$_3$), 3.60 (t, 2H, J=5.6 Hz, H$_1$), 3.14 (q, 2H, J=5.8 Hz, H$_2$), 1.29 (s, 9H, H$_4$);
$^{13}$C NMR (150 MHz, DMSO-d$_6$) δ 164.1, 155.7, 135.4, 134.4, 104.0, 77.7, 38.9, 37.5, 28.1;
HRMS (ESI) Calcd for C$_{15}$H$_{14}$N$_2$O$_4$I$_4$Na (M+Na)$^+$: 816.7030. Found: 816.7028.

Preparational Example 2

Preparation of Cyclized Neutral Phthalimide Derivative (10)

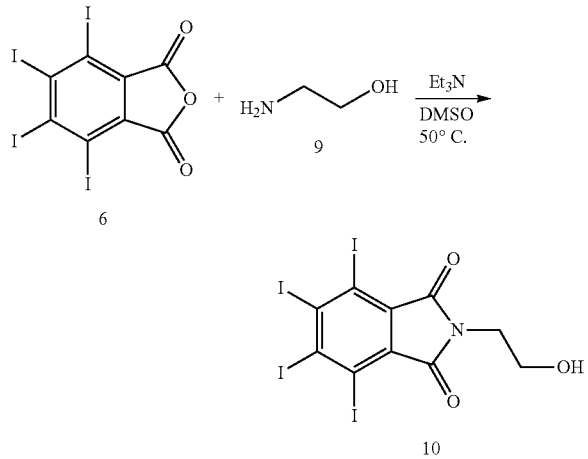

To a solution of Compound 6 (TIPN, 3.84 g, 5.89 mmol) and Compound 9 (ethanolamine, 300 mg, 4.91 mmol) in DMSO (8 mL) was added triethylamine (0.82 mL, 5.88 mmol). The reaction was heated at 50° C. and stirred for 19 hours under a dry argon atmosphere. The reaction mixture was passed through a SEC column (model: Bio-Beads S-X1, H 36 cm×O.D. 4.5 cm, manufacturer: Bio-Rad) in DMF to remove DMSO, concentrated under reduced pressure, and the crude product was chromatographed on silica gel (10:1 CH$_2$Cl$_2$/acetone) to give 1.11 g of Compound 10 (1.60 mmol, 33%) as a yellow powder.

R$_f$: 0.37 [silica gel, 10:1 CH$_2$Cl$_2$/acetone];
$^1$H NMR (600 MHz, DMSO-d$_6$) δ 3.62 (t, 2H, J=5.8 Hz, H$_1$), 3.55 (q, 2H, J=5.8 Hz, H$_2$);
$^{13}$C NMR (150 MHz, DMSO-d$_6$) δ 164.2, 135.5, 134.4, 104.0, 57.5, 41.3.

Example 1

Preparation of G1 PAMAM-mPEG$_{2000}$-TIPAA Conjugate (1c)

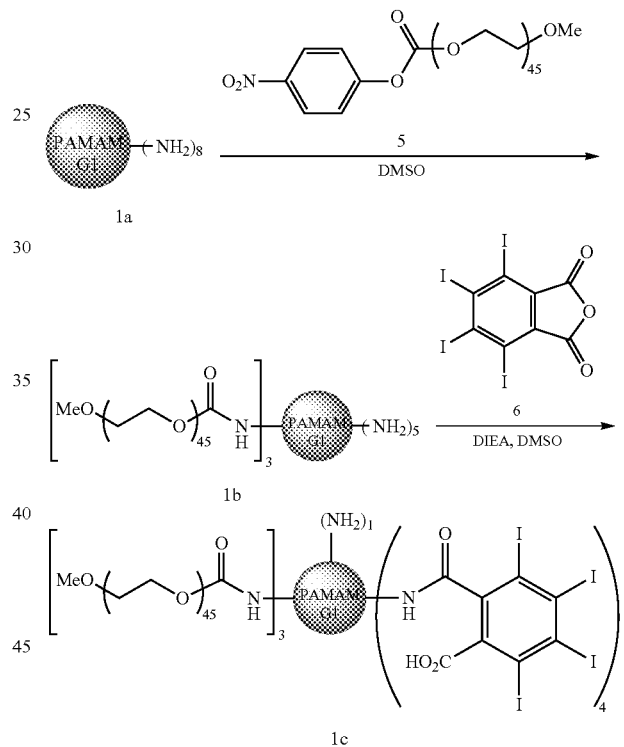

Step 1: Preparation of G1 PAMAM-mPEG$_{2000}$ Conjugate (1b)

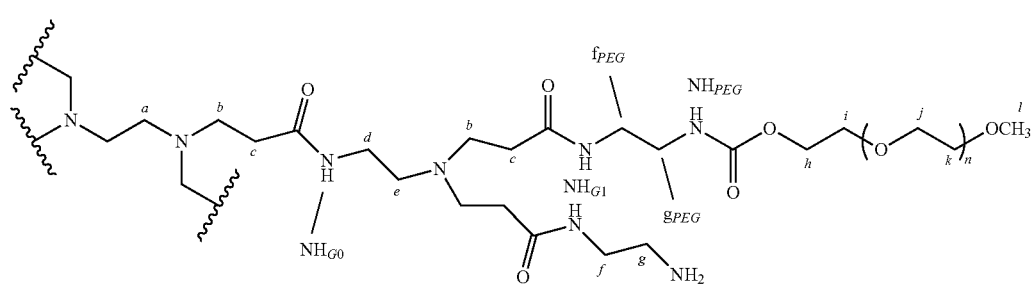

The commercial G1 PAMAM dendrimer (Compound 1a) purchased from Sigma-Aldrich Co. was dried in vacuo to remove methanol. To a stirred solution of Compound 1a (1.31 g, 0.916 mmol) in DMSO (100 mL) was added mPEG carbonate Compound 5 (4.95 g, 2.27 mmol) in one portion. The reaction mixture was stirred at room temperature for 2 days under a dry argon atmosphere, and then dialyzed (model: Spectra/Por Regenerated Cellulose (RC) membrane, MWCO 1000, manufacturer: Spectrum Laboratories) against methanol (×2, for 6 hours each) with stirring. After removal of the solvent under reduced pressure, the crude product was purified by a preparative SEC (model: Bio-Beads S-X1, H 40 cm×O.D. 4.5 cm, manufacturer: Bio-Rad) in DMF and dried in vacuo to give 5.65 g of Compound 1b.

$^1$H NMR (600 MHz, DMSO-$d_6$) δ 8.12-7.87 (m, NH$_{G0}$ and NH$_{G1}$), 7.22 (br s, 2.94H, NH$_{PEG}$ of major isomer), 6.80 (br s, 0.34H, NH$_{PEG}$ of minor isomer), 4.04 (t, 6.17H, J=4.7 Hz, H$_h$), 3.62-3.39 (m, 667.57H, H$_i$, H$_j$, and H$_k$), 3.24 (s, H$_l$), 3.10-2.99 (m, 33.53H, H$_d$, H$_f$, H$_{fPEG}$, and H$_{gPEG}$), 2.66-2.58 (m, 33.08H, H$_b$ and H$_g$), 2.43 (m, 11.86H, H$_e$ and H$_a$), 2.19 (m, 24.00H, H$_c$);

MS (MALDI-TOF, DHB matrix) M$_n$ 7698.11, M$_w$ 7747.40, PDI 1.01;

MS (MALDI-TOF, THAP matrix) M$_n$ 7757.35, M$_w$ 7795.41, PDI 1.00.

Step 2: Preparation of G1 PAMAM-mPEG$_{2000}$-TIPAA Conjugate (1c)

To a solution of Compound 1b (5.65 g) obtained in Step 1 and Compound 6 (TIPN, 5.90 g, 9.05 mmol) in DMSO (100 mL) was added N,N-diisopropylethylamine (DIEA, 2.40 mL, 13.8 mmol). The reaction mixture was stirred at room temperature for 2 days under a dry argon atmosphere. Next, TIPN (3.00 g, 4.60 mmol) was added additionally to the mixture in one portion and the reaction was continued to stir at room temperature for another 24 hours. The reaction mixture was dialyzed (model: Spectra/Por RC membrane, MWCO 1000, manufacturer: Spectrum Laboratories) against methanol (×2, for 6 hours each) with stirring. After removal of the solvent under reduced pressure, the crude product was purified by a preparative SEC (model: Bio-Beads S-X1, H 40 cm×O.D. 4.5 cm, manufacturer: Bio-Rad) in DMF. The combined residue was filtered through a SEC column (Sephadex LH-20, H 40 cm×O.D. 3.0 cm) to remove the remaining DMF. Subsequently, the product was dissolved in ethanol (80 mL) and the ethanolic solution was sterile-filtered through a syringe filter (model: Puradisc 25 Syringe Filter, pore size 0.45 μm, PTFE, manufacturer: Whatman). The filtrate was dried in vacuo extensively for 3 days to give 3.89 g of Compound 1c.

Iodine content (Inductively coupled plasma mass spectrometry, ICP-MS): 20.7%.

Example 2

Preparation of G2 PAMAM-mPEG$_{2000}$-TIPAA Conjugate (2c)

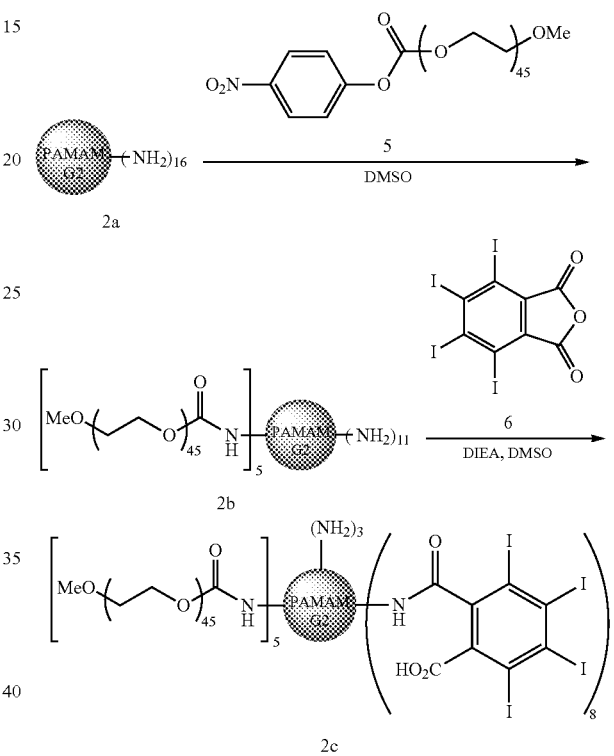

Step 1: Preparation of G2 PAMAM-mPEG$_{2000}$ Conjugate (2b)

2b

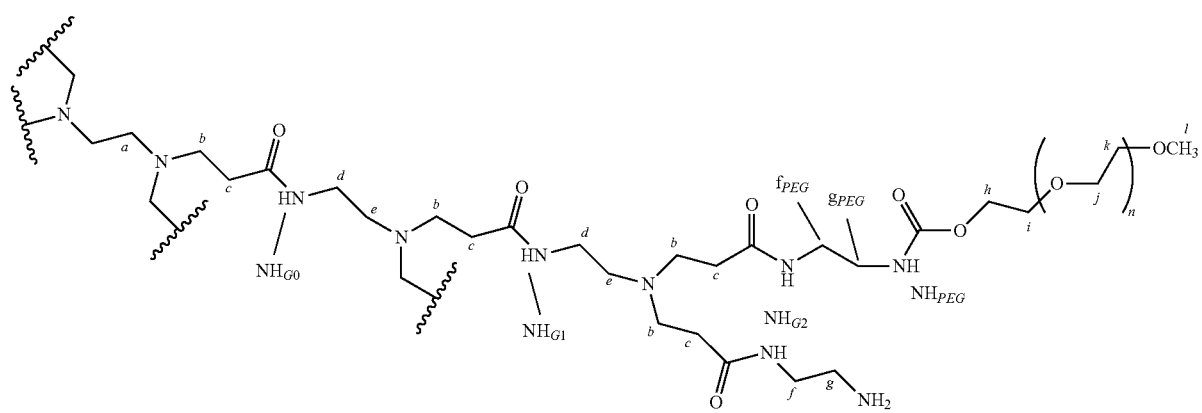

The commercial G2 PAMAM dendrimer (Compound 2a) purchased from Sigma-Aldrich Co. was dried in vacuo to remove methanol. To a stirred solution of Compound 2a (1.32 g, 0.405 mmol) in DMSO (90 mL) was added mPEG carbonate Compound 5 (3.94 g, 1.81 mmol) in one portion. The reaction mixture was stirred at room temperature for 2 days under a dry argon atmosphere, and then dialyzed (model: Spectra/Por RC membrane, MWCO 3500, manufacturer: Spectrum Laboratories) against methanol (×2, for 6 hours each) with stirring. After removal of the solvent under reduced pressure, the crude product was purified by a preparative SEC (model: Bio-Beads S-X1, H 40 cm×O.D. 4.5 cm, manufacturer: Bio-Rad) in DMF and dried in vacuo to give 5.20 g of Compound 2b.

$^1$H NMR (600 MHz, DMSO-d$_6$) δ 8.03-7.83 (m, NH$_{G0}$, NH$_{G1}$, and NH$_{G2}$), 7.21 (br s, 4.50H, NH$_{PEG}$ of major isomer), 6.80 (br s, 0.60H, NH$_{PEG}$ of minor isomer), 4.04 (t, 8.61H, J=4.6 Hz, H$_h$), 3.62-3.39 (m, 925.04H, H$_i$, H$_j$, and H$_k$), 3.24 (s, H$_l$), 3.10-3.00 (m, 70.07H, H$_d$, H$_f$, H$_{fPEG}$, and H$_{gPEG}$) 2.65 (m, 52.49H, H$_b$), 2.57 (m, 19.21H, H$_g$), 2.43 (m, 27.58H, H$_e$ and H$_a$), 2.20 (m, 56.00H, H$_c$);

MS (MALDI-TOF, THAP matrix) M$_n$ 11742.14, M$_w$ 11785.30, PDI 1.00.

Step 2: Preparation of G2 PAMAM-mPEG$_{2000}$-TIPAA Conjugate (2c)

To a solution of Compound 2b (5.20 g) obtained in Step 1 and Compound 6 (TIPN, 1.89 g, 2.90 mmol) in DMSO (94 mL) was added DIEA (0.80 mL, 4.6 mmol). The reaction mixture was stirred at room temperature for 2 days under a dry argon atmosphere. Next, TIPN (990 mg, 1.52 mmol) was added additionally to the mixture in one portion and the reaction was continued to stir at room temperature for another 24 hours. The reaction mixture was dialyzed (model: Spectra/Por RC membrane, MWCO 8000, manufacturer: Spectrum Laboratories) against methanol for 6 hours with stirring. After removal of the solvent under reduced pressure, the crude product was purified by a preparative SEC (model: Bio-Beads S-X1, H 40 cm×O.D. 4.5 cm, manufacturer: Bio-Rad) in DMF. The combined residue was filtered through a SEC column (Sephadex LH-20, H 40 cm×O.D. 3.0 cm) to remove the remaining DMF. Subsequently, the product was dissolved in ethanol (80 mL) and the ethanolic solution was sterile-filtered through a syringe filter (model: Puradisc 25 Syringe Filter, pore size 0.45 μm, PTFE, manufacturer: Whatman). The filtrate was dried in vacuo extensively for 3 days to give 3.04 g of Compound 2c.

Iodine content (ICP-MS): 23.0%.

Example 3

Preparation of G3 PAMAM-mPEG$_{2000}$-TIPAA Conjugate (3c)

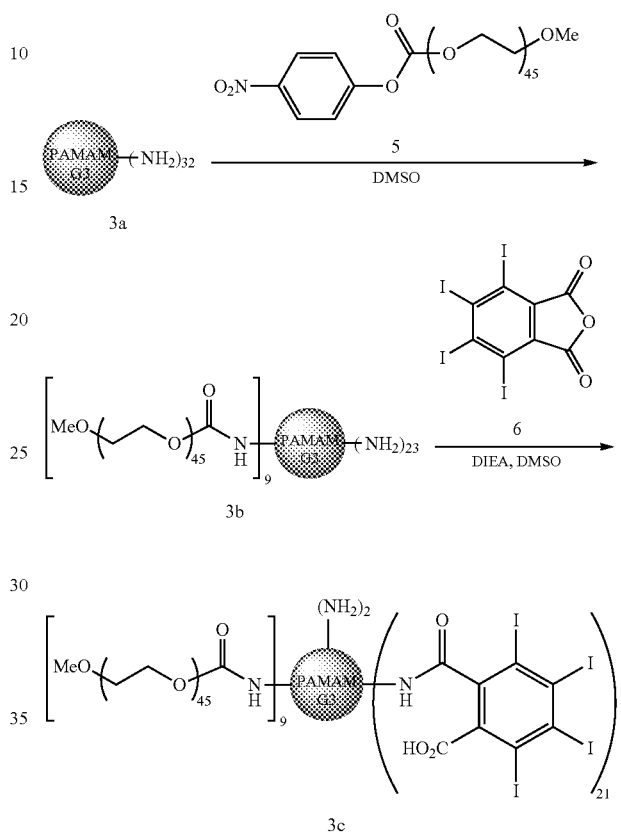

Step 1: Preparation of G3 PAMAM-mPEG$_{2000}$ Conjugate (3b)

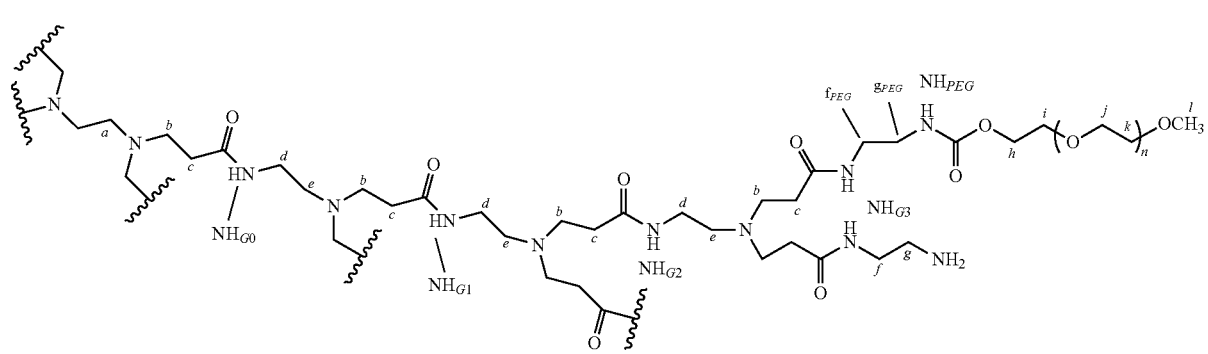

The commercial G3 PAMAM dendrimer (Compound 3a) purchased from Sigma-Aldrich Co. was dried in vacuo to remove methanol. To a stirred solution of Compound 3a (1.16 g, 0.168 mmol) in DMSO (112 mL) was added mPEG carbonate Compound 5 (3.27 g, 1.50 mmol) in one portion. The reaction mixture was stirred at room temperature for 2 days under a dry argon atmosphere, and then dialyzed (model: Spectra/Por RC membrane, MWCO 1000, manufacturer: Spectrum Laboratories) against methanol (×2, for 6 hours each) with stirring. After removal of the solvent under reduced pressure, the crude product was purified by a preparative SEC (model: Bio-Beads S-X1, H 40 cm×O.D. 4.5 cm, manufacturer: Bio-Rad) in DMF and dried in vacuo to give 3.29 g of Compound 3b.

$^1$H NMR (600 MHz, DMSO-d$_6$) δ 8.13-7.83 (m, NH$_{G0}$, NH$_{G1}$, NH$_{G2}$, and NH$_{G3}$), 7.22 (br s, 8.98H, NH$_{PEG}$ of major isomer), 6.80 (br s, 1.16H, NH$_{PEG}$ of minor isomer), 4.04 (t, 17.51H, J=4.5 Hz, H$_h$), 3.62-3.39 (m, 1846.66H, H$_i$, H$_j$, and H$_k$), 3.24 (s, H$_l$), 3.10-2.99 (m, 149.85H, H$_d$, H$_f$, H$_{fPEG}$, and H$_{gPEG}$) 2.66-2.59 (m, 146.61H, H$_b$ and H$_g$), 2.43 (m, 56.55H, H$_e$ and H$_a$), 2.20 (m, 120.00H, H$_c$);

MS (MALDI-TOF, DHB matrix) M$_n$ 21045.06, M$_w$ 22307.71, PDI 1.06.

Step 2: Preparation of G3 PAMAM-mPEG$_{2000}$-TIPAA Conjugate (3c)

To a solution of Compound 3b (3.24 g) obtained in Step 1 and Compound 6 (TIPN, 3.86 g, 5.92 mmol) in DMSO (100 mL) was added DIEA (1.50 mL, 8.61 mmol). The reaction mixture was stirred at room temperature for 2 days under a dry argon atmosphere. Next, TIPN (1.93 g, 2.96 mmol) was added additionally to the mixture in one portion and the reaction was continued to stir at room temperature for another 24 hours. The reaction mixture was dialyzed (model: Spectra/Por RC membrane, MWCO 1000, manufacturer: Spectrum Laboratories) against methanol for 6 hours with stirring. After removal of the solvent under reduced pressure, the crude product was purified by a preparative SEC (model: Bio-Beads S-X1, H 40 cm×O.D. 4.5 cm, manufacturer: Bio-Rad) in DMF. The combined residue was filtered through a SEC column (Sephadex LH-20, H 40 cm×O.D. 3.0 cm) to remove the remaining DMF. Subsequently, the product was dissolved in ethanol (80 mL) and the ethanolic solution was sterile-filtered through a syringe filter (model: Puradisc 25 Syringe Filter, pore size 0.45 μm, PTFE, manufacturer: Whatman). The filtrate was dried in vacuo extensively for 3 days to give 3.32 g of Compound 3c.

Iodine content (ICP-MS): 26.5%.

Example 4

Preparation of G4 PAMAM-mPEG$_{2000}$-TIPAA Conjugate (4c)

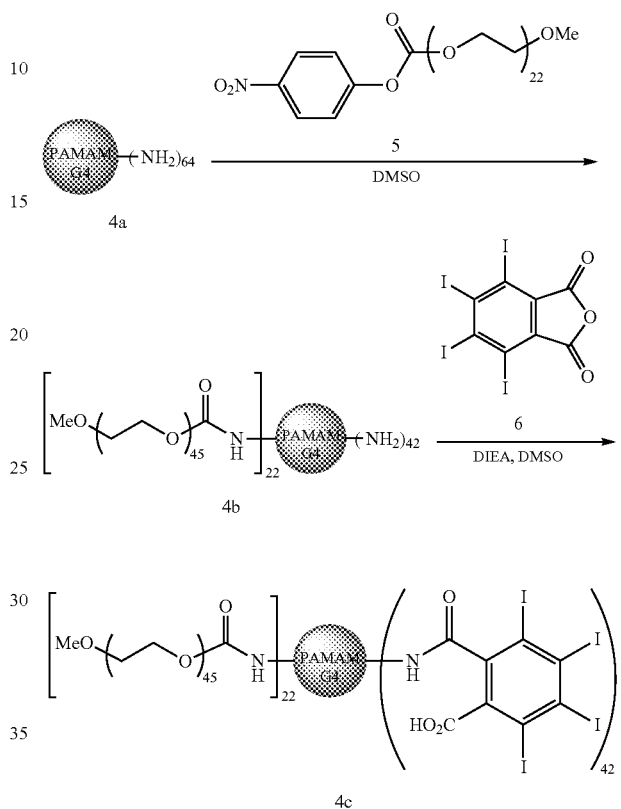

Step 1: Preparation of G4 PAMAM-mPEG$_{2000}$ Conjugate (4b)

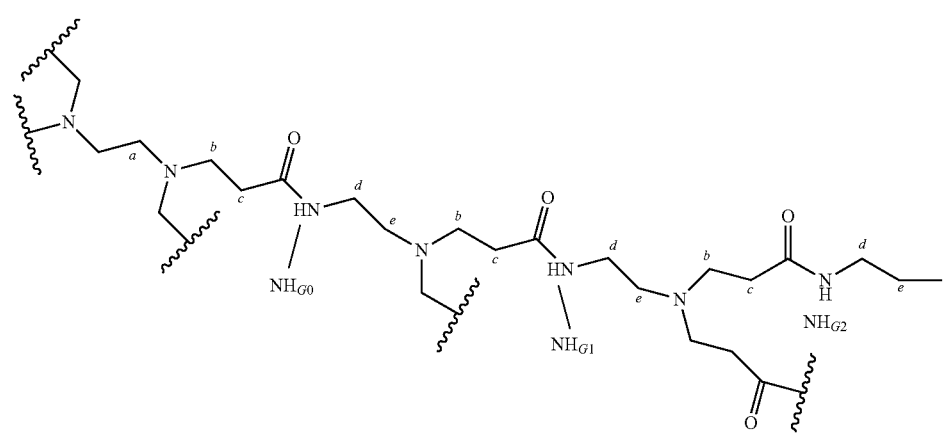

4b

-continued

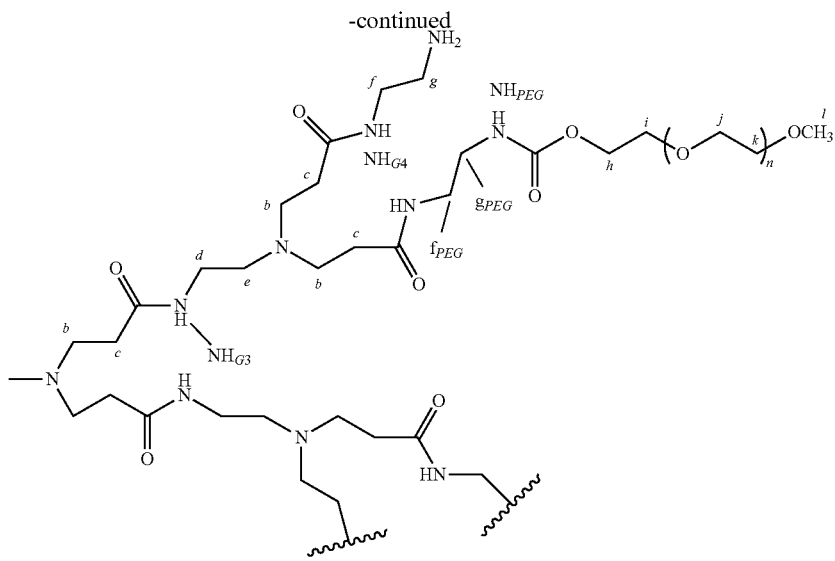

The commercial G4 PAMAM dendrimer (Compound 4a) purchased from Sigma-Aldrich Co. was dried in vacuo to remove methanol. To a stirred solution of Compound 4a (579 mg, 0.0407 mmol) in DMSO (27 mL) was added mPEG carbonate Compound 5 (1.94 g, 0.890 mmol) in one portion. The reaction mixture was stirred at room temperature for 2 days under a dry argon atmosphere, and then dialyzed (model: Spectra/Por RC membrane, MWCO 1000, manufacturer: Spectrum Laboratories) against methanol (×2, for 6 hours each) with stirring. After removal of the solvent under reduced pressure, the crude product was purified by a preparative SEC (model: Bio-Beads S-X1, H 40 cm×O.D. 4.5 cm, manufacturer: Bio-Rad) in DMF and dried in vacuo to give 1.67 g of Compound 4b.

$^1$H NMR (600 MHz, DMSO-d$_6$) δ 8.04-7.81 (m, NH$_{G0}$, NH$_{G1}$, NH$_{G2}$, NH$_{G3}$, and NH$_{G4}$), 7.22 (br s, 20.62H, NH$_{PEG}$ of major isomer), 6.81 (br s, 2.90H, NH$_{PEG}$ of minor isomer), 4.03 (t, 39.80H, J=4.5 Hz, H$_h$), 3.62-3.39 (m, 4330.96H, H$_i$, H$_j$, and H$_k$), 3.24 (s, H$_l$), 3.11-2.99 (m, 310.94H, H$_d$, H$_f$, H$_{fPEG}$, and H$_{gPEG}$), 2.68-2.61 (m, 299.21H, H$_b$ and H$_g$), 2.43 (m, 104.94H, H$_e$ and H$_a$), 2.20 (m, 248.00H, H$_c$);

MS (MALDI-TOF, DHB matrix) M$_n$ 44435.05, M$_w$ 46195.16, PDI 1.04.

Step 2: Preparation of G4 PAMAM-mPEG$_{2000}$-TIPAA Conjugate (4c)

To a solution of Compound 4b (1.63 g) obtained in Step 1 and Compound 6 (TIPN, 1.35 g, 2.07 mmol) in DMSO (32 mL) was added DIEA (0.54 mL, 3.10 mmol). The reaction mixture was stirred at room temperature for 2 days under a dry argon atmosphere. Next, TIPN (677 mg, 1.04 mmol) was added additionally to the mixture in one portion and the reaction was continued to stir at room temperature for another 24 hours. The reaction mixture was dialyzed (model: Spectra/Por RC membrane, MWCO 1000, manufacturer: Spectrum Laboratories) against methanol for 6 hours with stirring. After removal of the solvent under reduced pressure, the crude product was purified by a preparative SEC (model: Bio-Beads S-X1, H 40 cm×O.D. 4.5 cm, manufacturer: Bio-Rad) in DMF. The combined residue was filtered through a SEC column (Sephadex LH-20, H 40 cm×O.D. 3.0 cm) to remove the remaining DMF. Subsequently, the product was dissolved in ethanol (80 mL) and the ethanolic solution was sterile-filtered through a syringe filter (model: Puradisc 25 Syringe Filter, pore size 0.45 μm, PTFE, manufacturer: Whatman). The filtrate was dried in vacuo extensively for 3 days to give 1.27 g of Compound 4c.

Iodine content (ICP-MS): 25.2%.

Experimental Example 1

Cytotoxicity Assays

Human epithelial cervical cancer (HeLa) cell line was obtained from American Type Culture Collection (ATCC, Manassas, Va.) and maintained at 37° C. under a 5% carbon dioxide ($CO_2$) atmosphere in Dulbecco's modified eagle medium (DMEM, Gibco) supplemented with 10% fetal bovine serum (FBS), 50 U/mL penicillin, and 50 μg/mL streptomycin. Stock solutions of PAMAM-PEG$_{2000}$-TIPAA conjugate Compounds 1c-4c were prepared by dissolving 10 mg of each vacuum-dried solid sample in 1.0 mL of deionized water (Millipore Milli-Q) to make a 10 mg/mL solution. Each stock solution was sonicated briefly to ensure homogeneity. Serial dilutions were carried out using serum-free DMEM to prepare samples of the following concentrations: 1, 5, 10, 50, 100, and 500 μg/mL. HeLa cells were seeded in a flat bottomed 96-well plate (Corning Costar, Cambridge, Mass.) at a density of 1×10$^3$ cells per well and incubated for 24 hours at 37° C. under a 5% $CO_2$ atmosphere to allow cell attachment. Cells were treated with 100 μL of each dilution or 100 μL of serum-free DMEM (as a control) per well and incubated at 37° C. under a 5% $CO_2$ atmosphere for 24, 48, or 72 hours. The formulations were replaced with serum-free DMEM containing 5 mg/mL 3-(4,5-dimethylthiazol-2-yl)-2,5-diphenyltetrazolium bromide (MTT) and cells were incubated for additional 4 hours. MTT was removed by aspiration and DMSO (100 μL) was added to each well to dissolve the formazan crystals [Mosmann, T., J. Immunol. Methods 1983, 65, 55-63]. Absorbance was measured at 570 nm using a BioRad microplate reader, and the results are shown in FIG. 1. Assays were carried out in quadruplicates.

As illustrated in FIG. 1, four CT contrast media Compounds 1c, 2c, 3c, and 4c prepared in Examples 1 to 4 exhibited high cell survival rates of 88.5%, 88.4%, 88.4%, and 87.9%, respectively, under the harshest conditions tested (incubated for 72 hours at the concentration of the contrast media of 500 µg/mL), and thus, CT contrast media Compounds 1c, 2c, 3c, and 4c hardly exhibited cytotoxicity.

Therefore, the results herein suggest the excellent safety of the CT contrast media including the iodine-containing radial-shaped macromolecule according to the present invention.

Experimental Example 2

Micro-CT Imaging Evaluation of Contrast Media Solutions in Tubes

In order to investigate the degree of contrast enhancements of the contrast media compositions including Compounds 1c, 2c, 3c, and 4c prepared in Examples 1, 2, 3, and 4, respectively, as active ingredients for CT imaging, the following experiments were performed.

Preparation Step: Preparation of CT Contrast Media Compositions

Sample solutions for in vivo injections as CT contrast agents were prepared by dissolving each PAMAM-PEG$_{2000}$-TIPAA conjugate (Compound 1c, 2c, 3c, or 4c) at 250 mg/mL in the sterilized 20 mM Tris buffer (242 mg tromethamine and 10 mg EDTA dissolved in 100 mL of deionized water (Millipore Milli-Q), pH 7.4). The resulting solution was sonicated briefly to ensure homogeneity and stored at 4° C., if not used immediately. Before the injection to the animal, the contrast agent solutions were removed from the fridge, warmed to room temperature, and agitated by vortex.

The results of the viscosity (30° C.) and osmolality measurements of the CT contrast media solutions of the present invention are summarized in the following Table 1.

TABLE 1

| Compound | Viscosity (mPa · s, 30° C.) | Osmolality (mOsm/kg) |
|---|---|---|
| Example 1 | 15.32 ± 0.39 | 464.75 ± 3.59 |
| Example 2 | 16.47 ± 0.80 | 233.50 ± 9.75 |
| Example 3 | 16.15 ± 0.53 | 225.75 ± 1.26 |
| Example 4 | 16.31 ± 0.61 | 242.00 ± 4.08 |

In Table 1, the values are presented as the mean±standard deviation. Five independent measurements were made for each compound under the same conditions, and the mean and standard deviation were calculated after excluding the highest and lowest values (i.e., 3 data).

Micro-CT Imaging Evaluation of Contrast Media Solutions in Tubes

Prior to the in vivo injection of CT contrast media (250 mg/mL) including Compounds 1c, 2c, 3c, or 4c of Examples 1 to 4 prepared in the Preparation Step, 2D X-ray snapshot images of these solutions and two commercially available CT contrast media each for human or animal application were obtained using micro-CT to compare their relative X-ray absorption in tubes under the same conditions as a preliminary evaluation.

Here, "Iobrix" (TAEJOON PHARM Co., Ltd.), a small molecule-based CT contrast medium for human applications rapidly excreted after intravascular injection, and "Fenestra VC" (ART, Canada), an emulsion nanoparticle-based CT contrast medium for animal applications capable of relatively prolonged circulation after intravascular injection, were used as a positive control group. Overall, eight 250 µL-tubes were prepared each containing the following: 250 µL each of four CT contrast media prepared in the Preparation Step, 250 µL of "Fenestra VC", 250 µL of "Iobrix", 250 µL of 20 mM Tris buffer solution (pH 7.4, 0.1 mg/mL EDTA included) as a negative control group, and one empty tube as a negative control group. These eight tubes were then arranged side by side in parallel on the imaging bed of a NFR Polaris-G90 in vivo micro-CT scanner (manufacturer: NanoFocusRay), and 2D X-ray snapshot images were taken [imaging parameters: 60 kVp, 60 µA, 500 ms exposure time, field of view (FOV) 80.00×83.71 mm$^2$, 1.4× magnification]. The results thereof are presented in FIG. 2.

Figure 2:
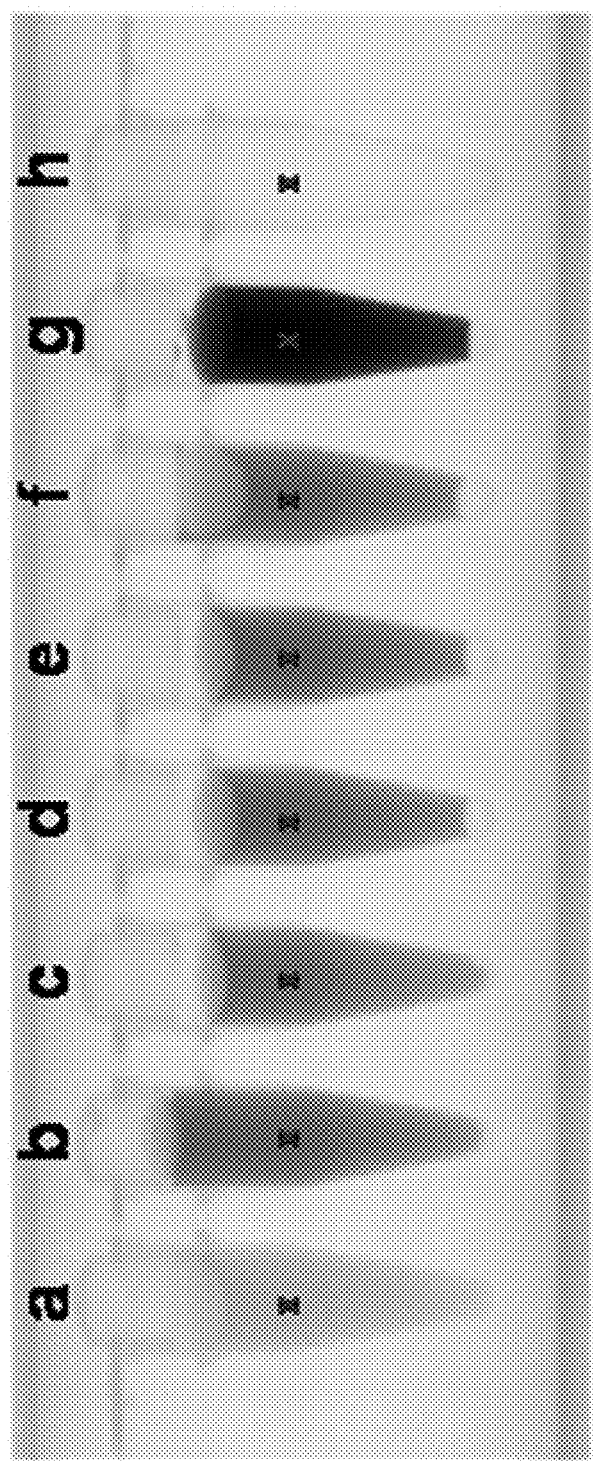
FIG. 2 illustrates 2D X-ray snapshot images of CT contrast media containing the compounds according to the embodiment of the present invention (a: 20 mM Tris buffer solution (pH 7.4, 0.1 mg/mL EDTA included); b: Fenestra VC; c: Example 1; d: Example 2; e: Example 3; f: Example 4; g: Iobrix; h: empty)

As illustrated in FIG. 2, X-ray transmittance (inversely proportional to X-ray absorbance) of all CT contrast media were much lower than those of a 20 mM Tris buffer solution (X-ray transmission intensity: 1359.5) and an empty tube (X-ray transmission intensity: 1676.5) used as a negative control group. Also among these, "Iobrix", a CT contrast medium for human applications which is rapidly excreted, exhibited the highest X-ray absorbance (X-ray transmission intensity: 198.0). "Fenestra VC" (X-ray transmission intensity: 866.0), a CT contrast medium for animal applications, and the CT contrast media including Compounds 1c, 2c, 3c, and 4c (X-ray transmission intensities: 904.5, 838.0, 826.5, and 827.0, in sequence) prepared in Examples 1 to 4 all exhibited similar X-ray absorption values in the 2D X-ray snapshot images in tubes.

Therefore, the results suggested that the CT contrast media including the iodine-containing radial-shaped macromolecule according to the present invention had sufficient contrast enhancement.

Experimental Example 3

In Vivo Micro-CT Imaging Evaluation

In order to investigate in vivo contrast enhancement over time after the administration of contrast media compositions including Compounds 1c to 4c prepared in Examples 1 to 4 as active ingredients, the micro-CT experiments were performed using small animals as described below.

Specifically, 6 to 8 weeks old healthy male C57BL/6 mice (Orient Bio, Korea) having the weight typically ranging from 15 g to 22 g were used as small animals. Each mouse was not fed water and food starting from approximately 12 hours before the injection of the contrast medium until the completion of CT imaging at 4 hours post-injection. The mice were fed water and food immediately after the completion of CT imaging at 4 hours post-injection. Before the injection of the contrast media, each mouse was anaesthetized in an induction chamber by administering 3% isoflurane in oxygen for about 5 minutes. Subsequently, the mouse was placed onto the imaging bed of a NFR Polaris-G90 in vivo micro-CT scanner (NanoFocusRay, Korea) lying in a prone position, and then the baseline (i.e., pre-contrast) scan was performed as a negative control group while being anesthesized by administering 1.5% isoflurane in oxygen [imaging parameters: 60 kVp, 60 µA, 500 ms exposure time, 360° scan angle, 600 scan number, 512 slices (i.e., image number); FOV: 80.00×83.71 mm$^2$ for low resolution whole-body imaging (1.4× magnification), 33.94×35.52 mm$^2$ for mid resolution chest and abdominal imaging (3.3× magnification), and 26.67×27.90 mm$^2$ for high resolution brain imaging (4.2× magnification)]. Next, the tail vein of the mouse was expanded by immersing the tail in a warm water for about 30 to 60 seconds while maintaining the mouse under anesthesia by administering 1.5% isoflurane in oxygen, and the corresponding amount of each contrast medium (15 mL/kg for the contrast media including the compounds of Examples 1 to 4, 10 mL/kg for "Fenestra VC", and 2.5 mL/kg for "Iobrix") was slowly injected into the tail vein of each mouse. Immediately after the injection of the contrast medium, the mouse was placed onto the imaging bed of a micro-CT scanner lying in a prone position, and the CT scan was performed at the corresponding resolution (low, mid, or high) while being anesthesized by administering 1.5% isoflurane in oxygen. This corresponds to the CT imaging at 0 hour (i.e., immediately after) post-injection.

Thereafter, CT scans were performed for each mouse at time points of 1 hour, 2 hours, 4 hours, 8 hours, 24 hours, and 48 hours post-injection in the same manner without the additional injection of the contrast medium. After each scan, the mouse was recovered by transferring to an individual cage in a strictly controlled environment of a constant temperature and humidity (22 to 25° C. and 50% to 60% humidity). For each contrast medium, whole-body CT scans were performed using 3 to 6 mice at the foregoing time points, and CT scans at 7 days post-injection were performed additionally using a mouse to see if most of the contrast medium was excreted.

Also, for the CT contrast media according to the present invention, expanded CT images were obtained by performing CT scans at higher resolutions using 1 or 2 mice under the same parameter settings to compare the contrast enhancement: at the mid resolution settings for the chest and abdominal region, and at the high resolution settings for the brain region. Immediately after each CT scan, the raw image files were reconstructed into a digital imaging and communications in medicine (DICOM) file format of 512×512 pixels in order to determine if any defect (i.e., error) is present in the axial images. Also, the 3D-rendered images were obtained from DICOM files using a Lucion software (Infinitt Healthcare, Korea).

Figure 4:
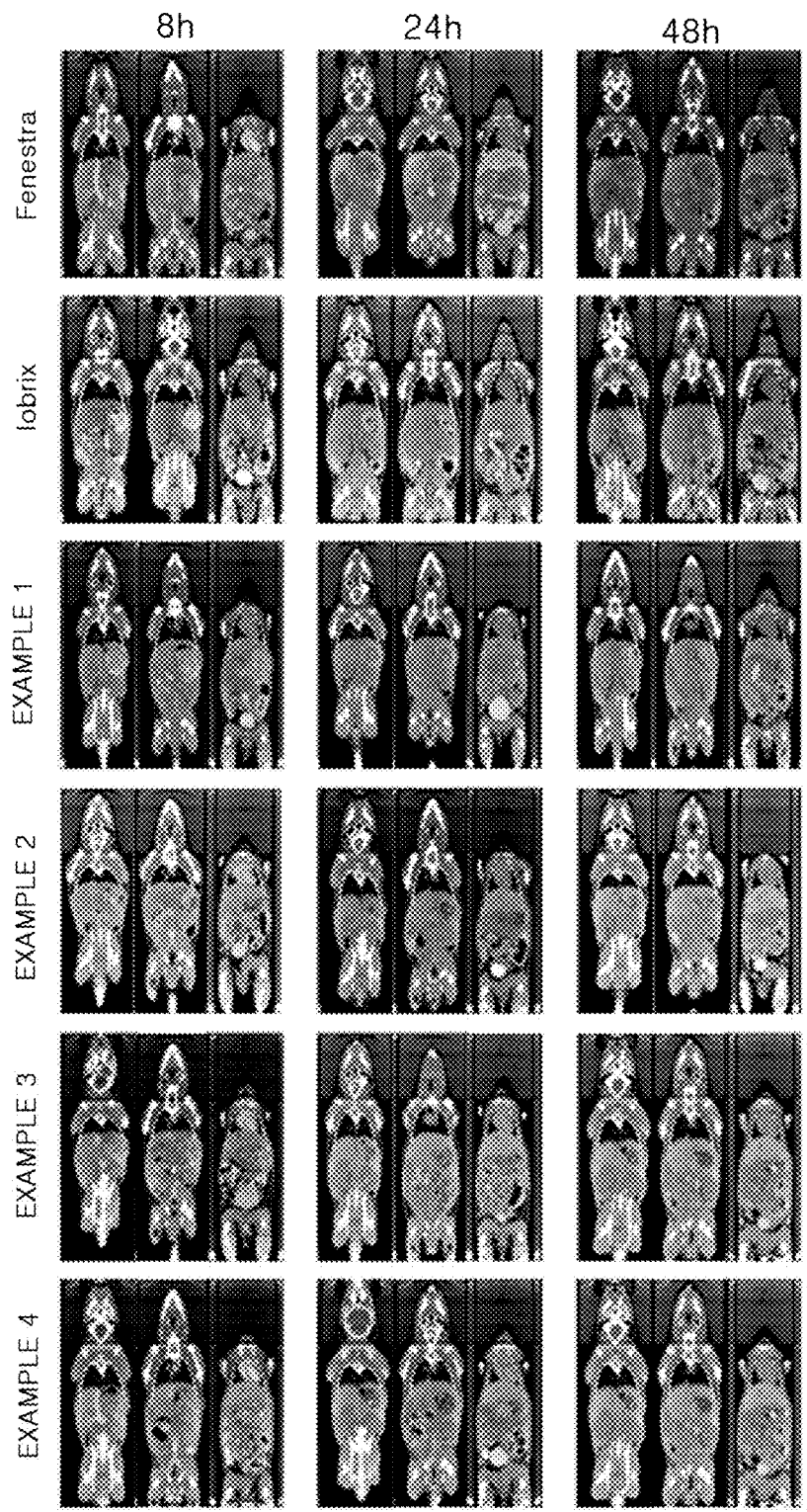
FIG. 4 illustrates the whole-body coronal CT images of mice administered with the CT contrast media containing the compounds according to the embodiment of the present invention obtained using micro-CT at the selected time points of 8, 24, and 48 hours post-injection.
Figure 5:
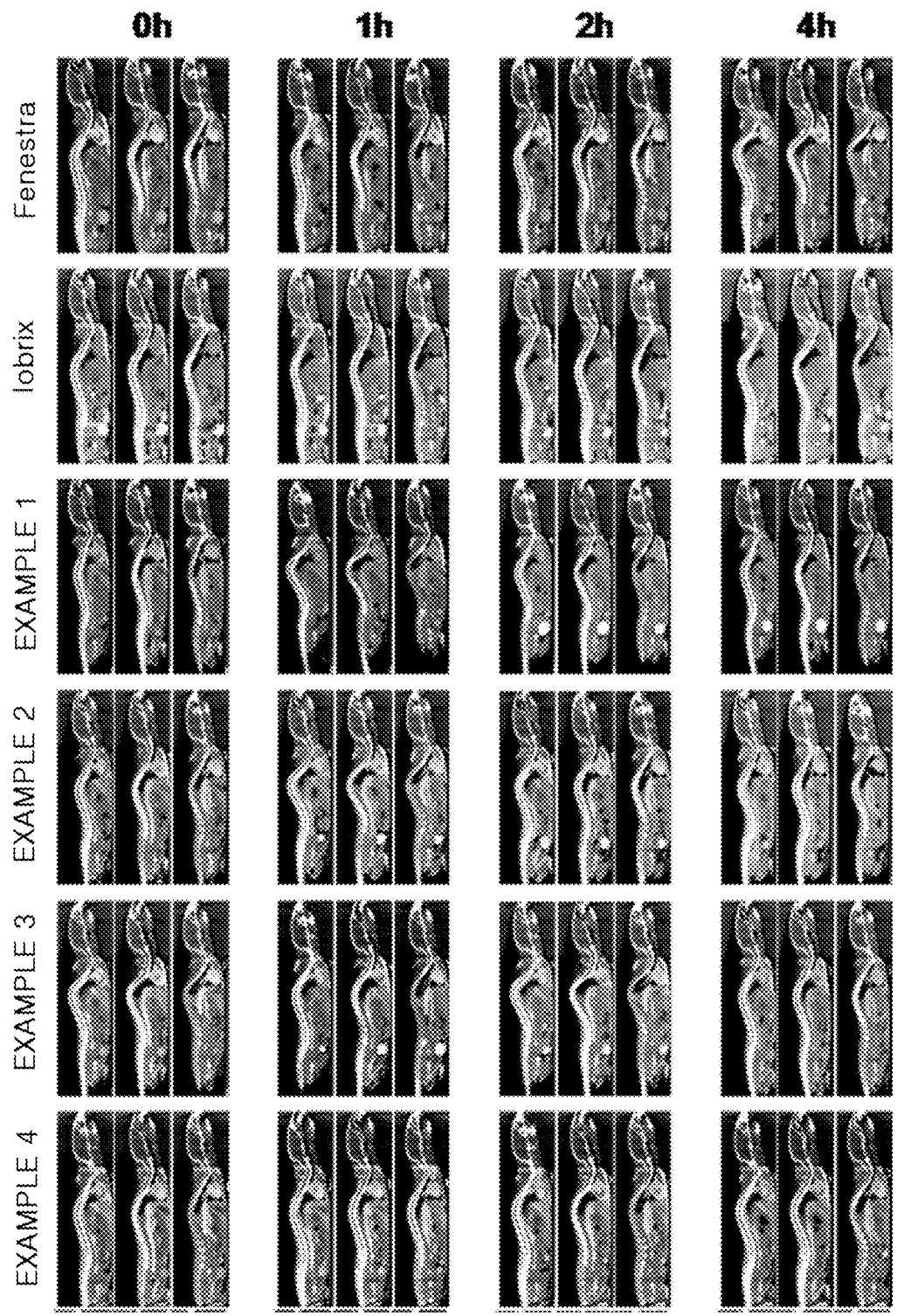
FIG. 5 illustrates the whole-body sagittal CT images of mice administered with the CT contrast media containing the compounds according to the embodiment of the present invention obtained using micro-CT at the selected time points of 0, 1, 2, and 4 hours post-injection.
Figure 6:
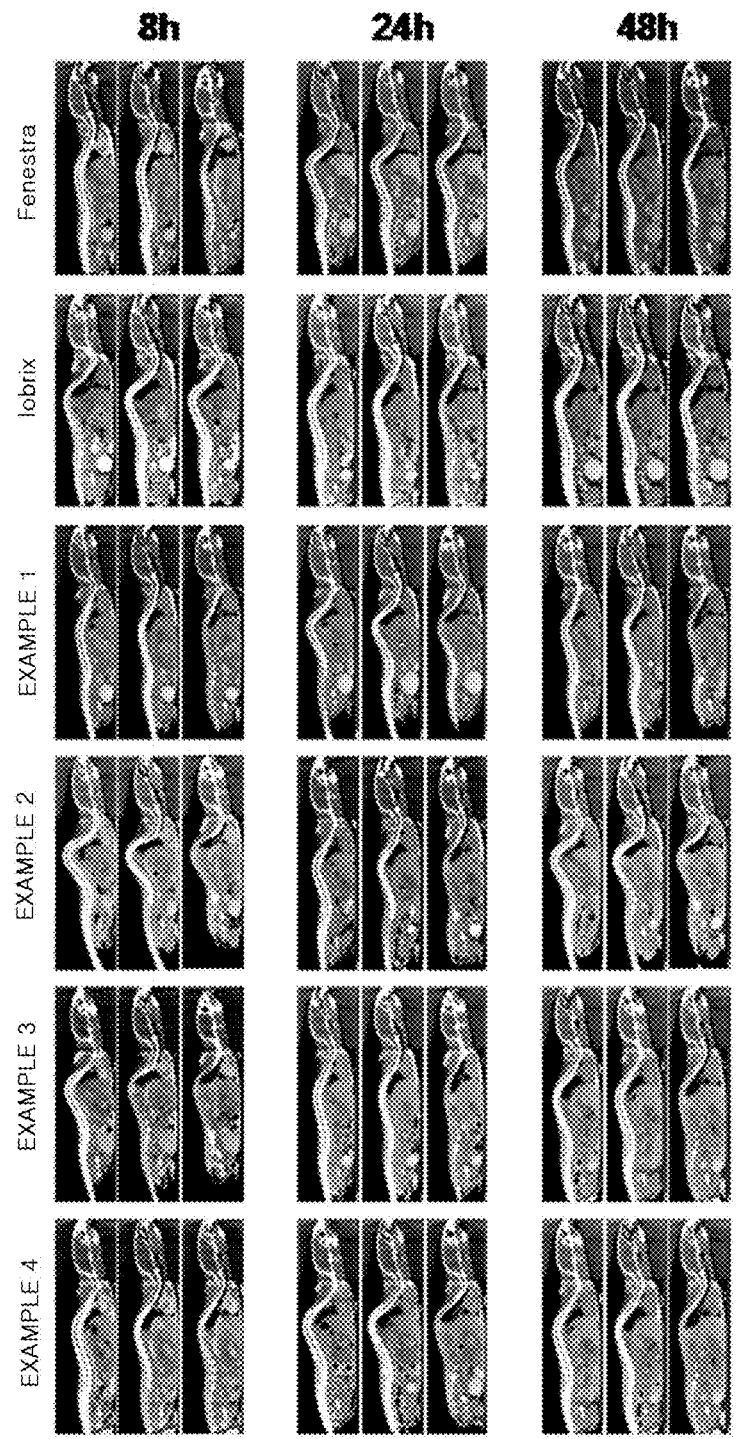
FIG. 6 illustrates the whole-body sagittal CT images of mice administered with the CT contrast media containing the compounds according to the embodiment of the present invention obtained using micro-CT at the selected time points of 8, 24, and 48 hours post-injection.

The whole-body coronal and sagittal CT images taken at the selected time points after the injection of four CT contrast media according to the present invention, and "Fenestra VC" and "Iobrix" used as a positive control group, into the tail vein of each mouse, are illustrated in FIGS. 3 and 4 (coronal) and FIGS. 5 and 6 (sagittal).

Figure 7:
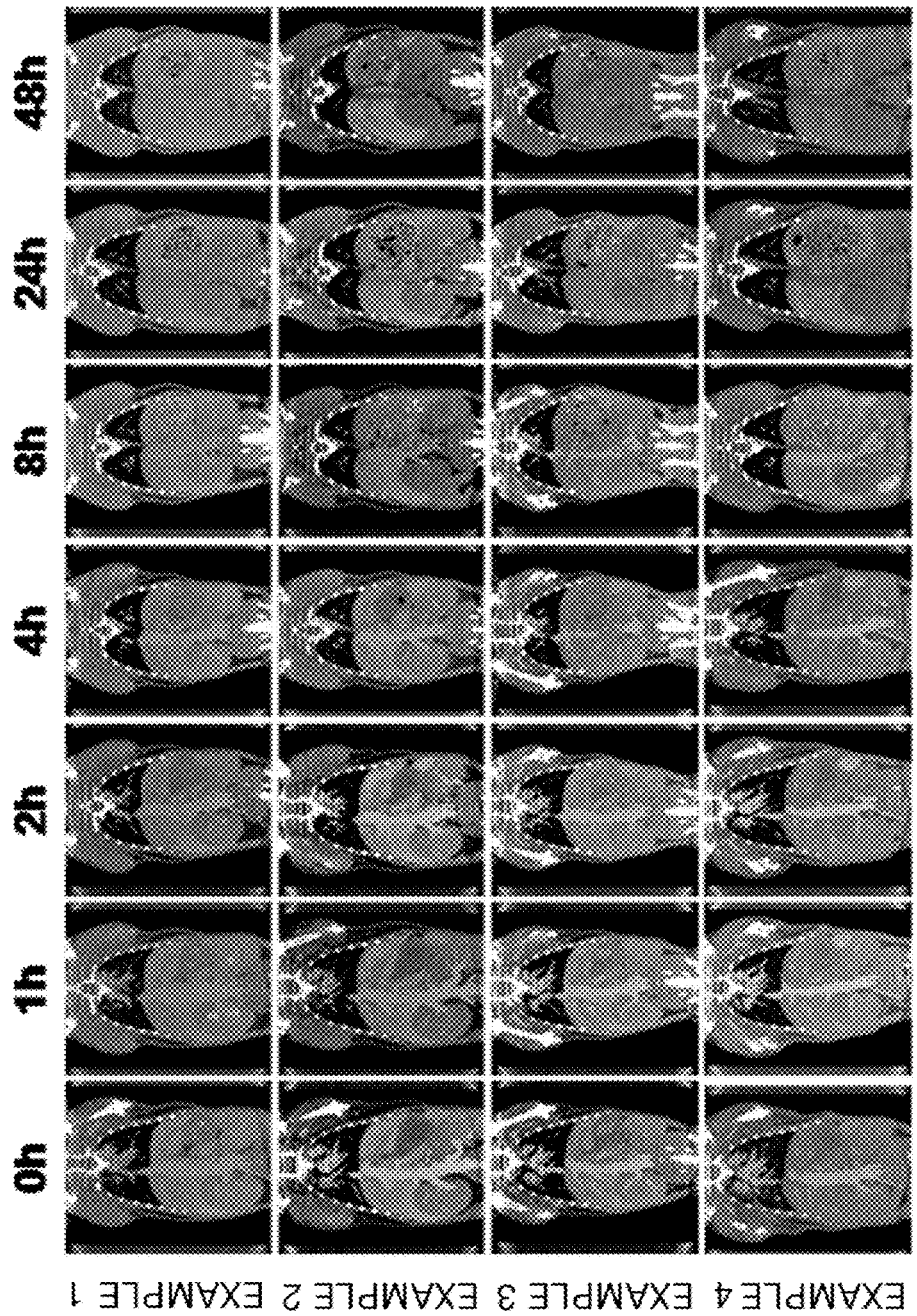
FIG. 7 illustrates the expanded coronal CT images for the chest and abdominal regions of mice administered with the CT contrast media containing the compounds according to the embodiment of the present invention obtained using micro-CT to compare the signal intensity (i.e., contrast enhancement) at the vena cava and liver.
Figure 8:
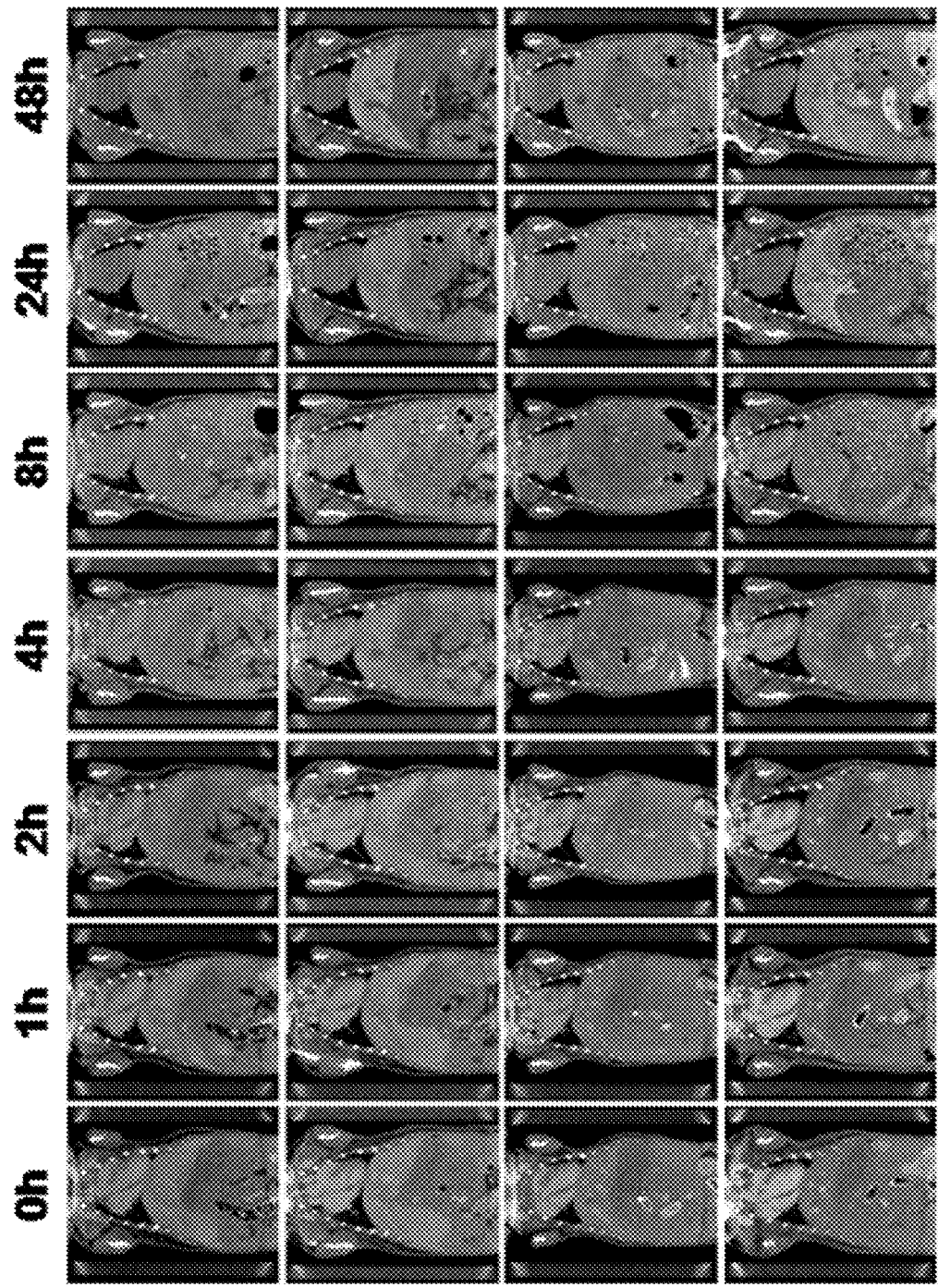
FIG. 8 illustrates the expanded coronal CT images for the chest and abdominal regions of mice administered with the CT contrast media containing the compounds according to the embodiment of the present invention obtained using micro-CT to compare the signal intensity (i.e., contrast enhancement) at the heart.
Figure 9:
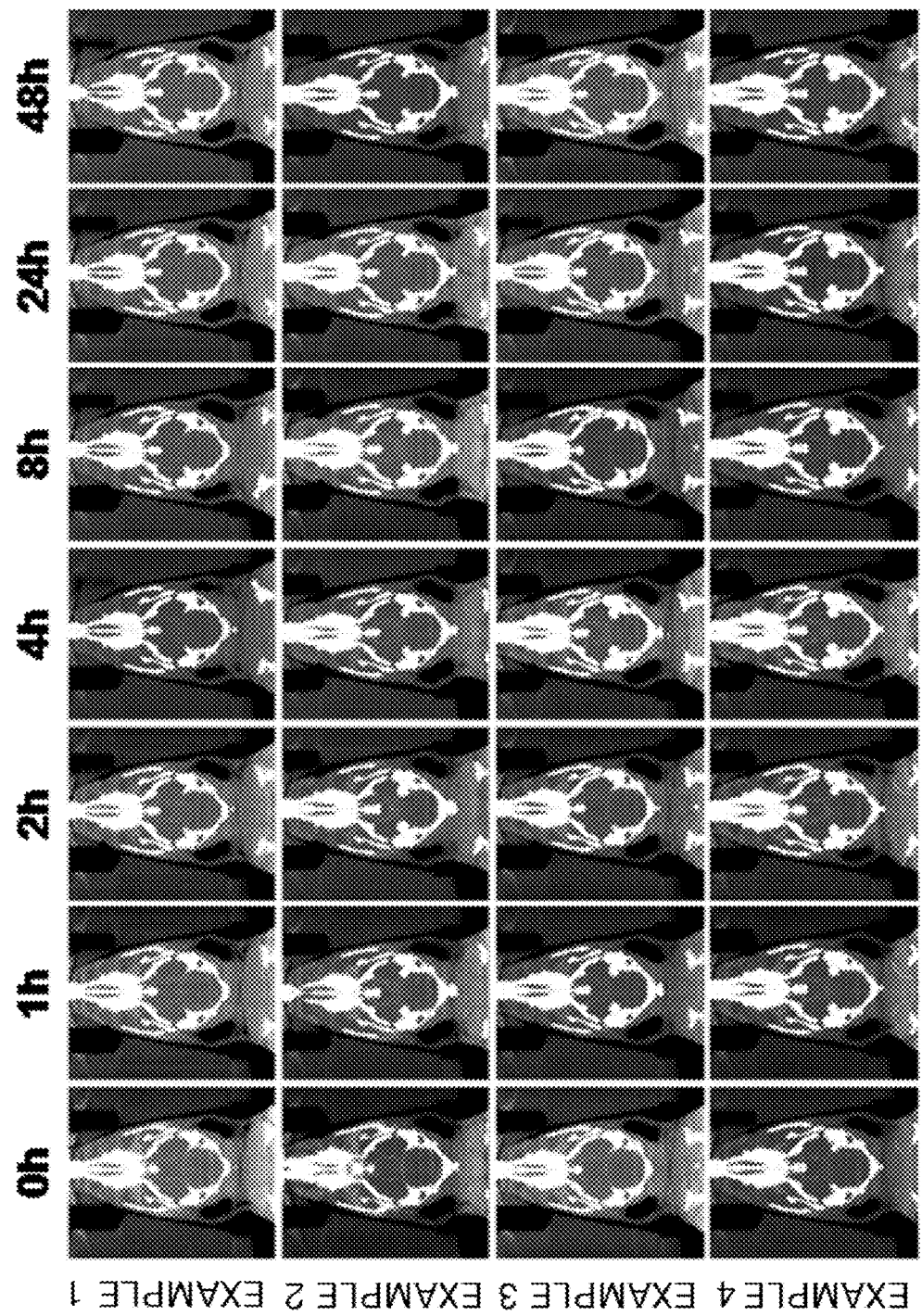
FIG. 9 illustrates the expanded coronal CT images for the brain region of mice administered with the CT contrast media containing the compounds according to the embodiment of the present invention obtained using micro-CT.
Figure 10:
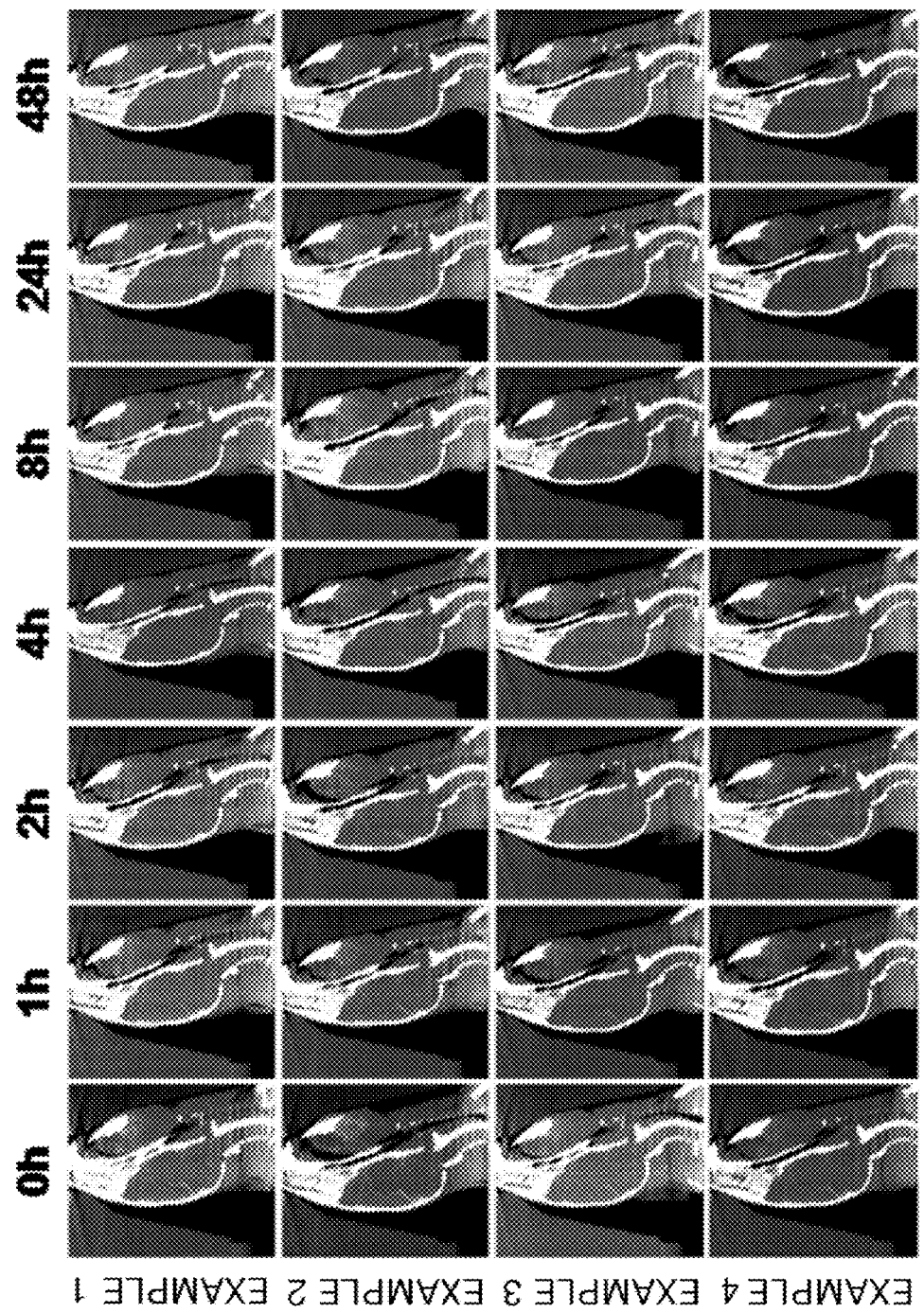
FIG. 10 illustrates the expanded sagittal CT images for the brain region of mice administered with the CT contrast media containing the compounds according to the embodiment of the present invention obtained using micro-CT.

Also, the expanded CT images for the chest and abdominal region (mid resolution) and the brain region (high resolution) taken at the selected time points after the injection of four CT contrast media according to the present invention in the tail vein of each mouse, are illustrated in FIGS. 7 and 8 (chest and abdomen) and FIGS. 9 and 10 (brain).

As illustrated in FIGS. 3 to 6, vascular regions of the mice injected with the CT contrast media are shown in light gray (bones are shown as very bright white color). Here, it is understood that "Iobrix", a small molecule-based CT contrast medium for human applications used as a positive control group, was excreted at a relatively fast rate through kidney within a few minutes after the injection (see the CT images at 0 hour post-injection). Also, it is understood that "Fenestra VC", an emulsion nanoparticle-based CT contrast medium for animal applications, initially exhibited a similar biodistribution profile as those of the CT contrast media including the compounds prepared in Examples 1 to 4, as shown by the similar level of contrast enhancement for up to 2 to 4 hours post-injection; however, at 24 hours post-injection, relatively higher contrast enhancement was observed in the liver for "Fenestra VC" in comparison to the CT contrast media according to the present invention, suggesting higher toxicity.

As illustrated in FIGS. 7 to 10, for the CT contrast media including the compounds prepared in Examples 1 to 4 of the present invention, intravascular circulation time increased as the molecular weight (i.e., size) increased. Also, for the contrast medium including Compound 1c prepared in Example 1 with a relatively low molecular weight, the route of excretion was mostly through kidney to bladder (see the CT images at 1 hour post-injection). In contrast, with increasing molecular weight (Example 2<Example 3<Example 4), the relative distribution in the liver compared to kidney (or bladder) has increased. In addition, relatively higher level of contrast enhancement was observed in the heart region for up to 24 hours post-injection for the CT contrast media including the compounds prepared in Examples 1 to 4 in comparison to that of "Fenestra VC". Furthermore, none of the mice injected with the CT contrast media of the present invention died during the CT experiments nor did show any damage in the organs such as liver and kidney as determined by the autopsy results and histological analysis.

Therefore, the results suggest that the CT contrast media including the iodine-containing radial-shaped macromolecule according to the present invention had sufficient contrast enhancement, prolonged circulation time, and proper excretion rate.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An iodine-containing radial-shaped macromolecule comprising:
 a core composed of a circular or spherical symmetric small molecular compound, or a radial-shaped macromolecule;
 an iodine-containing compound bound to the core directly or through a peptide; and
 a biocompatible polymer bound to the core directly or through a peptide, or directly bound to the iodine-containing compound bound to the core,
 wherein
 the iodine-containing radial-shaped macromolecule has a structure in which the biocompatible polymers form a protective layer to prevent the exposure of the core and the iodine-containing compound in vivo; and
 the core has one or more surface functional groups selected form the group consisting of amine, hydroxyl, hydroxylamine, carboxyl, carboxyhydrazide, hydrazine, thiol, azide, alkynyl, halogen, aldehyde, ketone, epoxy, 3-carbomethoxypyrrolidinone, and tri-($C_{1-4}$ alkoxy)-silyl, which is covalently linked to the iodine-containing compound, the peptide, or the biocompatible polymer.

2. The iodine-containing radial-shaped macromolecule as set forth in claim 1, wherein the circular or spherical symmetric small molecular compound constituting the core is any one selected from the group consisting of any one of the carbohydrates selected from the group consisting of α-, β-, and γ-cyclodextrin, glucose, galactose, mannose, and derivatives thereof; porphyrin and derivatives thereof; 1,4,7,10-tetraazacyclododecane-1,4,7,10-tetraacetic acid (DOTA) and derivatives thereof; a cyclic peptide formed by connecting two to four peptides selected from the group consisting of lysine, aspartic acid, glutamic acid, serine, cysteine, and tyrosine; and derivatives thereof.

3. The iodine-containing radial-shaped macromolecule as set forth in claim 1, wherein the radial-shaped macromolecule constituting the core is one selected from the group consisting of any one of dendrimers selected from the group consisting of a poly(amidoamine) (PAMAM) dendrimer, a polylysine dendrimer, a poly(propylene imine (PPI) dendrimer, a polyester dendrimer, a polyglutamic acid dendrimer; a polyaspartic acid dendrimer, a polyglycerol dendrimer, and a polymelamine dendrimer, any one of hyperbranched polymers selected from the group consisting of polylysine, polyester, polyglutamic acid, polyaspartic acid, and polyglycerol; any one of the star-shaped polymers selected from the group consisting of polyethylene glycol (PEG) and copolymer derivatives thereof; and derivatives thereof.

4. The iodine-containing radial-shaped macromolecule as set forth in claim 1, wherein the iodine-containing compound is any one selected from the group consisting of the following Chemical Formulae 2, 3, 4, and 10:

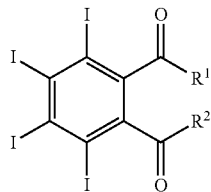

[Chemical Formula 2]

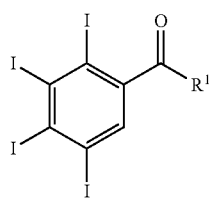

[Chemical Formula 3]

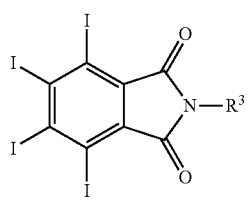

[Chemical Formula 4]

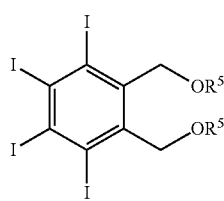

[Chemical Formula 10]

wherein $R^1$, $R^2$, and $R^3$ are each independently or selectively —$NH_2$, —$NHR^4$, —$NR^4_2$, —$NHNH_2$, —$NHNHR^4$, —$NHNR^4_2$, —OH, —$OR^4$, —SH, or —$SR^4$, $R^4$ is —H, -tert-butyloxycarbonyl (Boc), an unsubstituted or substituted straight or branched $C_{1-6}$ alkyl or heteroalkyl, or an unsubstituted or substituted $C_{5-7}$ aryl or heteroaryl, and $R^5$ is selected from the group consisting of —H, -tert-butyloxycarbonyl (Boc), an unsubstituted or substituted straight or branched $C_{1-6}$ alkyl or heteroalkyl, an unsubstituted or substituted $C_{5-7}$ aryl or heteroaryl, —(C=O)$R^4$, —(C=O)$OR^4$, —(C=O)$NHR^4$, and —(C=O)$NR^4_2$.

5. The iodine-containing radial-shaped macromolecule as set forth in claim 4, wherein the iodine compounds represented as the following Chemical Formula 1 and Chemical Formula 9 are precursors of the iodine-containing compounds of Chemical Formulae 2, 3, 4, and 10:

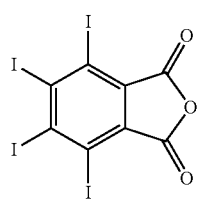

[Chemical Formula 1]

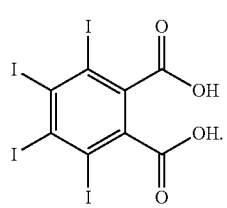

[Chemical Formula 9]

6. The iodine-containing radial-shaped macromolecule as set forth in claim 1, wherein the biocompatible polymer is any one selected from the group consisting of polyethylene glycol (PEG), hyaluronic acid, heparin, and derivatives thereof.

7. The iodine-containing radial-shaped macromolecule as set forth in claim 1, wherein the peptide is composed of 2 to 4 amino acid repeat units and may be selected from the group consisting of dilysine, trilysine, tetralysine, diglutamic acid, triglutamic acid, tetraglutamic acid, diaspartic acid, triaspartic acid, tetraaspartic acid, dicysteine, tricysteine, tetracysteine, diserine, triserine, and tetraserine.

8. The iodine-containing radial-shaped macromolecule as set forth in claim 1, wherein the linkages between the core, the iodine-containing compound, the peptide, or the biocompatible polymer are —NHC(=O)—, —C(=O)O—, —NHC(=O)NH—, —NHC(=O)O—, —NHC(=S)NH—, —C=N—NH—, —C=N—NHC(=O)—, —NH—, —S—, —SS—, —NHCH$_2$CH(OH)—, —O—, or

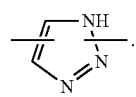

9. The iodine-containing radial-shaped macromolecule as set forth in claim 8, wherein both ends of the linkages are each bound to the core, the iodine-containing compound, the peptide, or the biocompatible polymer additionally through any one selected independently or selectively from the group consisting of —(CH$_2$)$_m$—, —(CH$_2$)$_m$(C=O)—, C$_{3-20}$ cycloalkyl-(CH$_2$)$_m$—, C$_{4-20}$ aryl-(CH$_2$)$_m$—, and —NH—CH$_2$CH$_2$—, wherein m is an integer between 0 and 10.

10. The iodine-containing radial-shaped macromolecule as set forth in claim 1, wherein an average molecular weight of the iodine-containing radial-shaped macromolecule is in the range of 8,000 Da to 150,000 Da.

11. The iodine-containing radial-shaped macromolecule as set forth in claim 1, wherein the iodine-containing radial-shaped macromolecule has structures of the following Chemical Formulae 5 to 8:

[Chemical Formula 5]

[Chemical Formula 6]

[Chemical Formula 7]

[Chemical Formula 8]

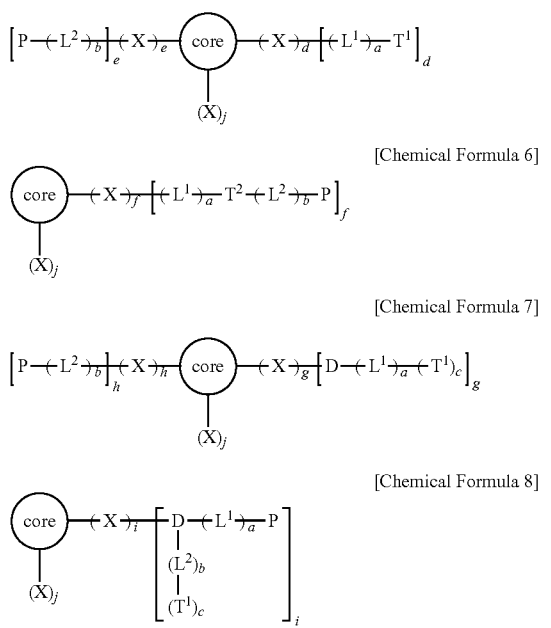

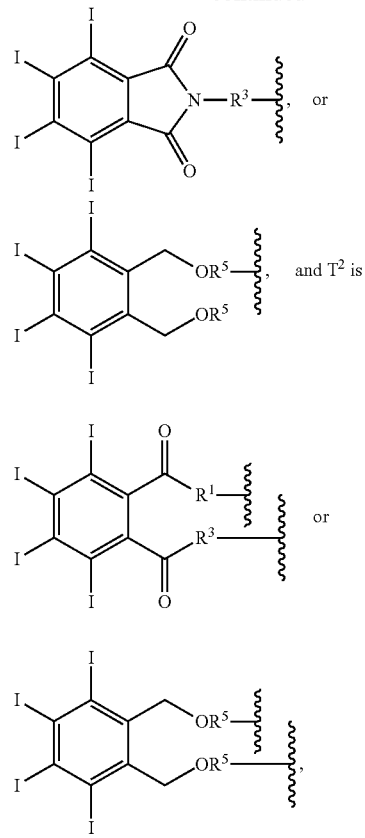

wherein the core is any one of carbohydrates selected from the group consisting of α-, β-, and γ-cyclodextrin, glucose, galactose, and mannose, and derivatives thereof; porphyrin and derivatives thereof; 1,4,7,10-tetraazacyclododecane-1,4,7,10-tetraacetic acid (DOTA) and derivatives thereof; a cyclic peptide formed by connecting two to four peptides selected from the group consisting of lysine, aspartic acid, glutamic acid, serine, cysteine, and tyrosine, and derivatives thereof; any one of dendrimers selected from the group consisting of a poly(amidoamine) (PAMAM) dendrimer, a polylysine dendrimer, a poly(propylene imine) (PPI) dendrimer, a polyester dendrimer, a polyglutamic acid dendrimer; a polyaspartic acid dendrimer, a polyglycerol dendrimer, and a polymelamine dendrimer; any one of hyperbranched polymers selected from the group consisting of polylysine, polyester, polyglutamic acid, polyaspartic acid, and polyglycerol; any one of the star-shaped polymers selected from the group consisting of polyethylene glycol (PEG) and copolymer derivatives thereof; and derivatives thereof, $T^1$ and $T^2$ are iodine-containing compounds, in which $T^1$ is

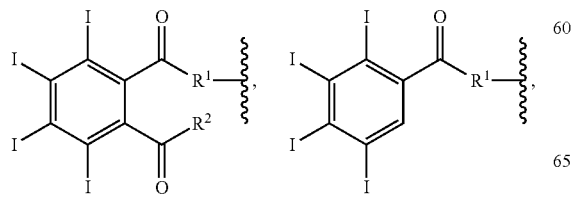

and wherein $R^1$ and $R^2$ are each independently or selectively —NH—, —NR$^4$—, —NNH$_2$—, —NNHR$^4$—, —NNR$^4_2$—, —O—, or —S—, $R^2$ is —NH$_2$, —NHR$^4$, —NR$^4_2$, —NHNH$_2$, —NHNHR$^4$, —NHNR$^4_2$, —OH, —OR$^4$, —SH, or —SR$^4$, $R^4$ is —H, -tert-butyloxycarbonyl (Boc), a straight or branched C$_{1-6}$ alkyl, or an unsubstituted or substituted C$_{5-7}$ aryl or heteroaryl, and $R^5$ is selected from the group consisting of —H, -tert-butyloxycarbonyl (Boc), an unsubstituted or substituted straight or branched C$_{1-6}$ alkyl or heteroalkyl, an unsubstituted or substituted C$_{5-7}$ aryl or heteroaryl, —(C=O)R$^4$, —(C=O)OR$^4$, —(C=O)NHR$^4$, and —(C=O)NR$^4_2$, D is a peptide composed of 2 to 4 amino acid repeat units and may be selected from the group consisting of dilysine, trilysine, tetralysine, diglutamic acid, triglutamic acid, tetraglutamic acid, diaspartic acid, triaspartic acid, tetraaspartic acid, dicysteine, tricysteine, tetracysteine, diserine, triserine, and tetraserine, P is PEG, hyaluronic acid, heparin, and derivatives thereof, X, as a surface functional group of the core and is amine, hydroxyl, hydroxylamine, carboxyl, carboxyhydrazide, hydrazine, thiol, azide, alkynyl, halogen, aldehyde, ketone, epoxy, 3-carbomethoxypyrrolidinone, and tri-(C$_{1-4}$ alkoxy)-silyl, $L^1$ and $L^2$ are linkages between the core, the iodine-containing compound ($T^1$ or $T^2$), the peptide (D), or the biocompatible polymer (P), and are —NHC(=O)—, —C(=O)O—, —NHC(=O)NH—, —NHC(=O)O—, —NHC(=S)NH—, —C=N—NH—, —C=N—NHC(=O)—, —NH—, —S—, —SS—, —NHCH$_2$CH(OH)—, —O—, or

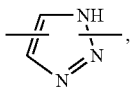

and both ends of the linkages are each bound to the core, the iodine-containing compound, the peptide, or the biocompatible polymer additionally through any one selected independently or selectively from the group consisting of —(CH$_2$)$_m$—, —(CH$_2$)$_m$(C=O)—, C$_{3-20}$ cycloalkyl-(CH$_2$)$_m$—, C$_{4-20}$ aryl-(CH$_2$)$_m$—, and —NH—CH$_2$CH$_2$—, wherein m is an integer between 0 and 10,
  a and b are each independently or selectively an integer of 0 or 1,
  c is an integer between 2 and 4,
  d, e, f, g, h, and i are each independently or selectively an integer between 2 and 60, and
  j is an integer between 1 and 10.

12. The iodine-containing radial-shaped macromolecule as set forth in claim 1, wherein, in the case that the biocompatible polymer is polyethylene glycol (PEG), a C$_{1-4}$ alkoxy group is the end group for polyethylene glycol (PEG), wherein the end group is located toward the outside from the core.

13. A method of preparing the iodine-containing radial-shaped macromolecule of claim 1, the method comprising:
  binding the biocompatible polymer to a portion of the surface functional groups of the core composed of a circular or spherical symmetric small molecular compound, or a radial-shaped macromolecule (step 1); and
  binding the iodine-containing compound to the unreacted surface functional groups of the core in step 1 directly or through a peptide (step 2).

14. A method of preparing the iodine-containing radial-shaped macromolecule of claim 1, the method comprising:
  binding the iodine-containing compound to a portion of the surface functional groups of the core composed of a circular or spherical symmetric small molecular compound, or a radial-shaped macromolecule (step 1); and
  binding the biocompatible polymer to the iodine-containing compound attached to the core in step 1 (step 2).

15. A method of preparing the iodine-containing radial-shaped macromolecule of claim 1, the method comprising:
  binding the iodine-containing compound to a biocompatible polymer through a peptide (step 1); and
  binding the iodine-containing compound bound to the biocompatible polymer through the peptide in step 1 to the surface functional groups of the core composed of a circular or spherical symmetric small molecular compound, or a radial-shaped macromolecule (step 2).

16. The method as set forth in claim 13, wherein the iodine-containing compound is any one selected from the group consisting of the following Chemical Formulae 1, 2, 3, 4, 9, and 10:

[Chemical Formula 1]

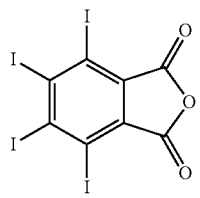

[Chemical Formula 2]

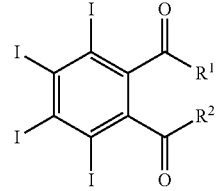

[Chemical Formula 3]

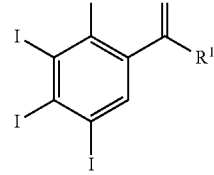

[Chemical Formula 4]

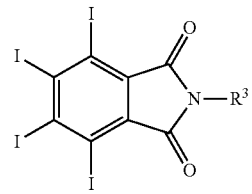

[Chemical Formula 9]

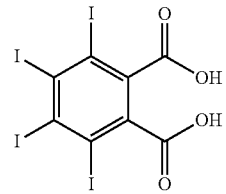

[Chemical Formula 10]

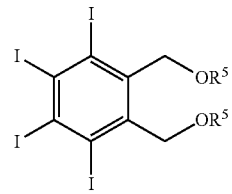

wherein R$^1$, R$^2$, and R$^3$ are each independently or selectively —NH$_2$, —NHR$^4$, —NR$^4{}_2$, —NHNH$_2$, —NHNHR$^4$, —NHNR$^4{}_2$, —OH, —OR$^4$, —SH, or —SR$^4$, R$^4$ is —H, -tert-butyloxycarbonyl (Boc), an unsubstituted or substituted straight or branched C$_{1-6}$ alkyl or heteroalkyl, or an unsubstituted or substituted C$_{5-7}$ aryl or heteroaryl, and R$^5$ is selected from the group consisting of —H, -tert-butyloxycarbonyl (Boc), an unsubstituted or substituted straight or branched C$_{1-6}$ alkyl or heteroalkyl, an unsubstituted or substituted C$_{5-7}$ aryl or heteroaryl, —(C=O)R$^4$, —(C=O)OR$^4$, —(C=O)NHR$^4$, and —(C=O)NR$^4{}_2$.

17. A computed tomography (CT) contrast medium composition comprising the iodine-containing radial-shaped macromolecule of claim 1 as an active ingredient.

18. The computed tomography (CT) contrast medium composition as set forth in claim 17, wherein the iodine content of the iodine-containing radial-shaped macromolecule is in the range of 15% to 50%.

* * * * *